US011561216B2

(12) United States Patent
Hyde et al.

(10) Patent No.: US 11,561,216 B2
(45) Date of Patent: Jan. 24, 2023

(54) APPARATUS FOR SUPPORTING AN ARRAY OF LAYERS OF AMPHIPHILIC MOLECULES AND METHOD OF FORMING AN ARRAY OF LAYERS OF AMPHIPHILIC MOLECULES

(71) Applicant: Oxford Nanopore Technologies PLC, Oxford (GB)

(72) Inventors: Jason Robert Hyde, Oxford (GB); James Anthony Clarke, Oxford (GB); Gaëlle Anne-Leonie Andreatta, Neuchâtel (CH)

(73) Assignee: Oxford Nanopore Technologies PLC, Oxford (GB)

( * ) Notice: Subject to any disclaimer, the term of this patent is extended or adjusted under 35 U.S.C. 154(b) by 0 days.

(21) Appl. No.: 16/404,107

(22) Filed: May 6, 2019

(65) Prior Publication Data
US 2019/0391128 A1  Dec. 26, 2019

Related U.S. Application Data

(63) Continuation of application No. 14/378,557, filed as application No. PCT/GB2013/050333 on Feb. 13, 2013, now Pat. No. 10,338,056.

(30) Foreign Application Priority Data

Feb. 13, 2012 (GB) ..................... 1202519

(51) Int. Cl.
*G01N 33/487* (2006.01)
*G01N 27/453* (2006.01)
(Continued)

(52) U.S. Cl.
CPC . *G01N 33/48721* (2013.01); *G01N 27/44791* (2013.01); *G01N 27/453* (2013.01);
(Continued)

(58) Field of Classification Search
CPC .......... G01N 33/48721; G01N 27/453; G01N 27/44791; B01L 2300/0819;
(Continued)

(56) References Cited

U.S. PATENT DOCUMENTS 3,799,743 A   3/1974  Alexander et al.
4,154,795 A   5/1979  Thorne
(Continued)

FOREIGN PATENT DOCUMENTS

AU   2003240941 A1   12/2003
CN       1303147 A    7/2001
(Continued)

OTHER PUBLICATIONS

Bruno Le Pioufle "Lipid Bilayer Microarray for Parallel Recording of Transmembrane Ion Currents" Analytical Chemistry 2008, 80, 328-332 (Year: 2008).*
(Continued)

*Primary Examiner* — Michael Y Sun
(74) *Attorney, Agent, or Firm* — Wolf, Greenfield & Sacks, P.C.

(57) ABSTRACT

An apparatus for supporting an array of layers of amphiphilic molecules, the apparatus comprising: a body, formed in a surface of the body, an array of sensor wells capable of supporting a layer of amphiphilic molecules across the sensor wells, the sensor wells each containing an electrode for connection to an electrical circuit, and formed in the surface of the body between the sensor wells, flow control wells capable of smoothing the flow of a fluid across the surface.

17 Claims, 8 Drawing Sheets

(51) Int. Cl.
  *G01N 27/447* (2006.01)
  *C12Q 1/6869* (2018.01)
  *B01L 3/00* (2006.01)
(52) U.S. Cl.
  CPC .......... *B01J 2219/00317* (2013.01); *B01J 2219/00585* (2013.01); *B01J 2219/00599* (2013.01); *B01J 2219/00653* (2013.01); *B01J 2219/00725* (2013.01); *B01L 3/5027* (2013.01); *B01L 3/5088* (2013.01); *B01L 3/50273* (2013.01); *B01L 3/502707* (2013.01); *B01L 2300/0819* (2013.01); *B01L 2400/0421* (2013.01); *B01L 2400/0427* (2013.01); *B01L 2400/0472* (2013.01); *C12Q 1/6869* (2013.01)
(58) Field of Classification Search
  CPC ........... B01L 2400/0472; B01L 3/5027; B01L 3/5088; B01L 2400/0421; B01L 2400/0427; B01L 3/50273; B01L 3/502707; B01J 2219/00599; B01J 2219/00653; B01J 2219/00725; B01J 2219/00317; B01J 2219/00585; C12Q 1/6869
  See application file for complete search history.

(56) References Cited

U.S. PATENT DOCUMENTS

| | | |
|---|---|---|
| 5,234,566 A | 8/1993 | Osman et al. |
| 5,403,451 A | 4/1995 | Riviello et al. |
| 5,503,803 A | 4/1996 | Brown et al. |
| 6,056,922 A | 5/2000 | Ikematsu |
| 6,300,141 B1 | 10/2001 | Segal et al. |
| 6,479,288 B1 | 11/2002 | Laffafian et al. |
| 6,483,931 B2 | 11/2002 | Kalnitsky et al. |
| 6,503,452 B1 | 1/2003 | Boxer et al. |
| 6,699,697 B2 | 3/2004 | Klemic et al. |
| 6,863,833 B1 | 3/2005 | Bloom et al. |
| 6,913,697 B2 | 7/2005 | Lopez et al. |
| 6,916,488 B1 | 7/2005 | Meier et al. |
| 7,077,939 B1 | 7/2006 | Crooks et al. |
| 7,144,486 B1 | 12/2006 | Fritsch et al. |
| 7,169,272 B2 | 1/2007 | Fritsch et al. |
| 7,745,116 B2 | 6/2010 | Williams |
| 7,939,270 B2 | 5/2011 | Holden et al. |
| 8,124,191 B2 | 2/2012 | Ervin et al. |
| 8,461,854 B2 | 6/2013 | Chen et al. |
| 9,546,400 B2 | 1/2017 | Turner et al. |
| 9,613,247 B2 | 4/2017 | Yang |
| 9,678,056 B2 | 6/2017 | Turner et al. |
| 9,734,382 B2 | 8/2017 | Wang et al. |
| 9,927,398 B2 | 3/2018 | Reid et al. |
| 10,036,065 B2 | 7/2018 | Jones |
| 10,338,056 B2 | 7/2019 | Hyde et al. |
| 10,416,117 B2 | 9/2019 | Reid et al. |
| 10,549,274 B2 | 2/2020 | Brown et al. |
| 10,814,298 B2 | 10/2020 | Hyde et al. |
| 11,084,015 B2 | 8/2021 | Hyde et al. |
| 11,097,269 B2 | 8/2021 | Goto et al. |
| 2002/0074227 A1 | 6/2002 | Nisch et al. |
| 2002/0123048 A1 | 9/2002 | Gau |
| 2002/0144905 A1 | 10/2002 | Schmidt |
| 2003/0015422 A1 | 1/2003 | Fritsch et al. |
| 2003/0075445 A1 | 4/2003 | Woudenberg et al. |
| 2003/0098248 A1 | 5/2003 | Vogel et al. |
| 2003/0111340 A1 | 6/2003 | Cheng et al. |
| 2003/0148401 A1 | 8/2003 | Agrawal et al. |
| 2003/0224523 A1 | 12/2003 | Thornberg et al. |
| 2004/0022677 A1 | 2/2004 | Wohlstadter et al. |
| 2004/0096358 A1 | 5/2004 | Blankstein et al. |
| 2004/0171169 A1 | 9/2004 | Kallury et al. |
| 2005/0014162 A1 | 1/2005 | Barth et al. |
| 2005/0133101 A1 | 6/2005 | Chung et al. |
| 2005/0230272 A1* | 10/2005 | Lee .................... G01N 33/5438 205/792 |
| 2005/0279634 A1 | 12/2005 | Ozaki et al. |
| 2006/0079009 A1 | 4/2006 | Salmon et al. |
| 2006/0163063 A1 | 7/2006 | Picollet-Dahan et al. |
| 2006/0194331 A1 | 8/2006 | Pamula et al. |
| 2006/0257941 A1 | 11/2006 | McDevitt et al. |
| 2007/0035308 A1 | 2/2007 | Ide |
| 2007/0161101 A1 | 7/2007 | Takeuchi |
| 2007/0275480 A1* | 11/2007 | Brander ................ G01N 33/68 436/501 |
| 2008/0254995 A1 | 10/2008 | Kim et al. |
| 2009/0072332 A1 | 3/2009 | Dekker et al. |
| 2009/0142504 A1 | 6/2009 | Ervin et al. |
| 2009/0167288 A1* | 7/2009 | Reid ................. B01L 3/502707 324/72 |
| 2010/0035349 A1 | 2/2010 | Bau et al. |
| 2010/0147450 A1 | 6/2010 | Takeuchi et al. |
| 2010/0190253 A1 | 7/2010 | Tazaki et al. |
| 2010/0196203 A1 | 8/2010 | Sanghera et al. |
| 2010/0304980 A1 | 12/2010 | Takeuchi et al. |
| 2011/0120871 A1 | 5/2011 | Reid et al. |
| 2011/0121840 A1 | 5/2011 | Sanghera et al. |
| 2011/0214991 A1 | 9/2011 | Kim et al. |
| 2011/0274737 A1* | 11/2011 | Palmaz .................. A61L 31/16 424/423 |
| 2011/0287414 A1 | 11/2011 | Chen et al. |
| 2011/0318774 A1 | 12/2011 | Larsen |
| 2012/0010085 A1 | 1/2012 | Rava et al. |
| 2013/0048499 A1 | 2/2013 | Mayer et al. |
| 2013/0071932 A1 | 3/2013 | Itchoda et al. |
| 2013/0140192 A1 | 6/2013 | Behrends et al. |
| 2013/0196442 A1 | 8/2013 | Momose et al. |
| 2013/0207205 A1 | 8/2013 | Chen |
| 2013/0217106 A1 | 8/2013 | Jones et al. |
| 2013/0270521 A1 | 10/2013 | Peng et al. |
| 2013/0309776 A1 | 11/2013 | Drndic et al. |
| 2014/0190833 A1 | 7/2014 | Lieber et al. |
| 2014/0243214 A1 | 8/2014 | Haga et al. |
| 2014/0255921 A1 | 9/2014 | Moysey et al. |
| 2014/0296083 A1 | 10/2014 | Brown et al. |
| 2014/0318964 A1 | 10/2014 | Dunbar et al. |
| 2014/0329693 A1 | 11/2014 | Reid et al. |
| 2014/0335512 A1 | 11/2014 | Moysey et al. |
| 2014/0346059 A1 | 11/2014 | Akeson |
| 2014/0346515 A1 | 11/2014 | Yanagi et al. |
| 2015/0014160 A1 | 1/2015 | Hyde et al. |
| 2015/0027885 A1 | 1/2015 | Rajaraman et al. |
| 2015/0065354 A1 | 3/2015 | Moysey et al. |
| 2015/0191709 A1 | 7/2015 | Heron et al. |
| 2015/0198611 A1 | 7/2015 | Ostrowski et al. |
| 2015/0204763 A1 | 7/2015 | Stelzle et al. |
| 2015/0218629 A1 | 8/2015 | Heron et al. |
| 2015/0232923 A1 | 8/2015 | Drndic et al. |
| 2015/0265994 A1 | 9/2015 | Hyde et al. |
| 2015/0268256 A1 | 9/2015 | Sanghera et al. |
| 2015/0300986 A1 | 10/2015 | Reid et al. |
| 2016/0040230 A1 | 2/2016 | Akeson |
| 2016/0231307 A1 | 8/2016 | Xie |
| 2016/0257942 A1 | 9/2016 | Bruce et al. |
| 2017/0189906 A1 | 7/2017 | Moll et al. |
| 2017/0326550 A1 | 11/2017 | Brown et al. |
| 2017/0363577 A1 | 12/2017 | Reid et al. |
| 2018/0321188 A1 | 11/2018 | Reid et al. |
| 2019/0210021 A1 | 7/2019 | Waterman |
| 2019/0242913 A1 | 8/2019 | Sanghera et al. |
| 2020/0292521 A1 | 9/2020 | Xie et al. |
| 2021/0086160 A1 | 3/2021 | Hyde et al. |
| 2021/0170403 A1 | 6/2021 | Waterman |
| 2021/0300750 A1 | 9/2021 | Waterman |
| 2022/0023819 A1 | 1/2022 | Hyde et al. |

FOREIGN PATENT DOCUMENTS

| | | |
|---|---|---|
| CN | 1434461 | 8/2003 |
| CN | 1500555 A | 6/2004 |
| CN | 101078704 | 11/2007 |
| CN | 100448007 C | 12/2008 |

(56) References Cited

FOREIGN PATENT DOCUMENTS

| | | |
|---|---|---|
| CN | 101490277 A | 7/2009 |
| CN | 100571871 C | 12/2009 |
| CN | 102263104 A | 11/2011 |
| CN | 203466320 U | 9/2013 |
| CN | 103370617 A | 10/2013 |
| CN | 103995035 A | 8/2014 |
| CN | 205828393 U | 12/2016 |
| CN | 106457247 A | 2/2017 |
| DE | 102010022929 A1 | 12/2011 |
| EP | 0532215 A2 | 3/1993 |
| EP | 1110084 A1 | 6/2001 |
| EP | 1120469 A2 | 8/2001 |
| EP | 1419818 A1 | 5/2004 |
| EP | 1535667 A1 | 6/2005 |
| EP | 1669746 A1 | 6/2006 |
| EP | 1677102 | 7/2006 |
| EP | 1688742 | 8/2006 |
| EP | 1710578 | 10/2006 |
| EP | 1712909 A1 | 10/2006 |
| EP | 1779921 A1 | 5/2007 |
| EP | 2219032 A1 | 8/2010 |
| GB | 2237390 | 5/1991 |
| GB | 2446823 | 8/2008 |
| JP | S5-274882 A | 6/1977 |
| JP | 4014773 A2 | 1/1992 |
| JP | 4127066 A2 | 4/1992 |
| JP | 4-215052 | 8/1992 |
| JP | 7307172 A2 | 11/1995 |
| JP | 2004-158330 A2 | 6/2004 |
| JP | 2005-98718 | 4/2005 |
| JP | 2005-164276 A | 6/2005 |
| JP | 2005-300460 A | 10/2005 |
| JP | 2005-539242 | 12/2005 |
| JP | 2006-312141 | 11/2006 |
| JP | 2008-194573 | 8/2008 |
| JP | 2009-128206 A | 6/2009 |
| JP | 2010186677 A2 | 8/2010 |
| JP | 2012-247231 A | 12/2012 |
| JP | 2013-242247 A | 12/2013 |
| JP | 2014-190891 A | 10/2014 |
| JP | 2015-064373 A | 4/2015 |
| KR | 10-2017-0012367 | 2/2017 |
| WO | WO 1988/008534 A1 | 11/1988 |
| WO | WO 1994/25862 A1 | 11/1994 |
| WO | WO 1997/16545 A1 | 5/1997 |
| WO | WO 1998/58248 | 12/1998 |
| WO | WO 1999/013101 A1 | 3/1999 |
| WO | WO 2000/013014 A1 | 3/2000 |
| WO | WO 2000/25121 A1 | 5/2000 |
| WO | WO 2000/28312 | 5/2000 |
| WO | WO 2001/059447 A1 | 8/2001 |
| WO | WO 2002/24862 A2 | 3/2002 |
| WO | WO 2002/29402 A2 | 4/2002 |
| WO | WO 2002/035221 A1 | 5/2002 |
| WO | WO 2002/082046 A2 | 10/2002 |
| WO | WO 2003/052420 A2 | 6/2003 |
| WO | WO 2005/040783 A1 | 5/2005 |
| WO | WO 2005/124888 A1 | 12/2005 |
| WO | WO 2006/012571 A1 | 2/2006 |
| WO | WO 2006/076703 A2 | 7/2006 |
| WO | WO 2006/100484 | 9/2006 |
| WO | WO 2006/104639 | 10/2006 |
| WO | WO 2006/113550 | 10/2006 |
| WO | WO 2006/138160 A2 | 12/2006 |
| WO | WO 2007/028003 A2 | 3/2007 |
| WO | WO 2007/049576 A1 | 5/2007 |
| WO | WO 2007/116978 A1 | 10/2007 |
| WO | WO 2007/127327 | 11/2007 |
| WO | WO 2007/132002 A1 | 11/2007 |
| WO | WO 2008/012552 A1 | 1/2008 |
| WO | WO 2008/054611 A2 | 5/2008 |
| WO | WO 2008/102120 | 8/2008 |
| WO | WO 2008/102121 | 8/2008 |
| WO | WO 2008/124107 A1 | 10/2008 |
| WO | WO 2008/137008 A2 | 11/2008 |
| WO | WO 2008/156041 A1 | 12/2008 |
| WO | WO 2009/024775 A1 | 2/2009 |
| WO | WO 2009/035647 A1 | 3/2009 |
| WO | WO 2009/077734 A2 | 6/2009 |
| WO | WO 2010/086603 A1 | 8/2010 |
| WO | WO 2010/122293 | 10/2010 |
| WO | WO 2010/142954 A1 | 12/2010 |
| WO | WO 2011/046706 A1 | 4/2011 |
| WO | WO 2011/067559 A1 | 6/2011 |
| WO | WO 2011/118211 A1 | 9/2011 |
| WO | WO 2011/154114 A2 | 12/2011 |
| WO | WO 2012/033524 A2 | 3/2012 |
| WO | WO 2012/042226 A2 | 4/2012 |
| WO | WO 2012/107778 A2 | 8/2012 |
| WO | WO 2012/138357 A1 | 10/2012 |
| WO | WO 2013/041878 A1 | 3/2013 |
| WO | WO 2013/057495 A2 | 4/2013 |
| WO | WO 2013/121193 A2 | 8/2013 |
| WO | WO 2013/121224 A1 | 8/2013 |
| WO | WO 2013/123379 A2 | 8/2013 |
| WO | WO 2013/153359 A1 | 10/2013 |
| WO | WO 2014/013260 A1 | 1/2014 |
| WO | WO 2014/019603 A1 | 2/2014 |
| WO | WO 2014/064443 A2 | 5/2014 |
| WO | WO 2014/064444 A1 | 5/2014 |
| WO | WO 2014/158665 A1 | 10/2014 |
| WO | WO 2015/183871 A1 | 12/2015 |
| WO | WO 2015/193076 A1 | 12/2015 |
| WO | WO 2016/034591 A2 | 3/2016 |
| WO | WO 2016/059427 A1 | 4/2016 |
| WO | WO 2016/127007 A2 | 8/2016 |
| WO | WO 2016/172724 A1 | 10/2016 |
| WO | WO 2016/187519 A1 | 11/2016 |
| WO | WO 2017/061600 A1 | 4/2017 |
| WO | WO 2018/007819 A1 | 1/2018 |
| WO | WO 2019/063959 A1 | 4/2019 |

OTHER PUBLICATIONS

[No Author Listed] Avanti Polar Lipids, Inc. Avanti Polar Lipids—Preparations of Liposomes. Www.avantilipids.com 5 pages. Jul. 1, 2014.

Aghdaei et al., Formation of artificial lipid bilayers using droplet dielectrophoresis. Lab Chip. Oct. 2008;8(10):1617-20. doi: 10.1039/b807374k. Epub Aug. 13, 2008.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Anrather et al., Supported membrane nanodevices. J Nanosci Nanotechnol. Jan.-Feb. 2004;4(1-2):1-22.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006; 128(5):1705-10.

Baaken et al., Planar microelectrode-cavity array for high-resolution and parallel electrical recording of membrane ionic currents. Lab Chip. Jun. 2008;8(6):938-44. doi: 10.1039/b800431e. Epub Apr. 16, 2008.

Bezrukov et al., Counting polymers moving through a single ion channel. Nature. Jul. 28, 1994;370(6487):279-81.

Bruggemann et al., Microchip technology for automated and parallel patch-clamp recording. Small. Jul. 2006;2(7):840-6.

Cheng et al., Discrete membrane arrays. J Biotechnol. Sep. 2000;74(3):159-74.

Cheng et al., Single Ion Channel Sensitivity in Suspended Bilayers on Micromachined Supports. Langmuir. 2001;17(4):1240-1242.

Danelon et al., Cell membranes suspended across nanoaperture arrays. Langmuir. Jan. 3, 2006;22(1):22-5.

Devereux et al., A comprehensive set of sequence analysis programs for the VAX. Nucleic Acids Res. Jan. 11, 1984;12(1 Pt 1):387-95.

Estes et al., Electroformation of giant liposomes from spin-coated films of lipids. Colloids Surf B Biointerfaces. May 10, 2005;42(2):115-23.

(56) References Cited

OTHER PUBLICATIONS

Fraikin et al., A high-throughput label-free nanoparticle analyser. Nat Nanotechnol. 2011;6(5):308-313. doi:10.1038/nnano.2011.24.

Funakoshi et al., Lipid bilayer formation by contacting monolayers in a microfluidic device for membrane protein analysis. Anal Chem. Dec. 15, 2006;78(24):8169-74.

Garstecki et al., Formation of droplets and bubbles in a microfluidic T-junction-scaling and mechanism of break-up. Lab Chip. Mar. 2006;6(3):437-46. Epub Jan. 25, 2006. Erratum in: Lab Chip. May 2006;6(5):693.

Gonzalez-Perez et al., Biomimetic triblock copolymer membrane arrays: a stable template for functional membrane proteins. Langmuir. 2009;25(18):10447-10450. doi:10.1021/la902417m.

Hasanzadeh et al., Room-temperature ionic liquid-based electrochemical nanobiosensors. Trends Anal Chem. Dec. 2012;41:58-74.

Heron et al., Simultaneous measurement of ionic current and fluorescence from single protein pores. J Am Chem Soc. Feb. 11, 2009;131(5):1652-3. doi: 10.1021/ja808128s.

Hirano et al., Lipid Bilayers at Gel/Gel Interface for Ion Channel Recordings. Surf. Sci. Nanotech. 2008;6:130-133.

Holden et al., Functional bionetworks from nanoliter water droplets. J Am Chem Soc. Jul. 11, 2007;129(27):8650-5. Epub Jun. 16, 2007.

Horn, Avoiding Evaporation, Ibidi Application Note 12, Mar. 29, 2012, pp. 1-3.

Hovis et al., Patterning and Composition Arrays of Supported Lipid Bilayers by Microcontact Printing. Langmuir. 2001;17:3400-3405.

Hromada et al., Single molecule measurements within individual membrane-bound ion channels using a polymer-based bilayer lipid membrane chip. Lab Chip. Apr. 2008;8(4):602-8. doi:10.1039/b716388f. Epub Feb. 29, 2008.

Ide et al., A novel method for artificial lipid-bilayer formation. Biosens Bioelectron. Oct. 15, 2005;21(4):672-7. Epub Jan. 26, 2005.

Ivanov et al., DNA tunneling detector embedded in a nanopore. Nano Lett. 2011;11(1):279-285. doi:10.1021/nl103873a.

Jeon et al., Long-term storable and shippable lipid bilayer membrane platform. Lab Chip. Oct. 2008;8(10):1742-4. doi: 10.1039/b807932c. Epub Aug. 22, 2008.

Jung et al., Detecting protein-ligand binding on supported bilayers by local pH modulation. J Am Chem Soc. Jan. 28, 2009;131(3):1006-14. doi: 10.1021/ja804542p.

Kam et al., Spatially Selective Manipulation of Supported Lipid Bilayers by Laminar Flow: Steps Toward Biomembrane Microfluidic. Langmuir. 2003;19(5):1624-1631.

Kasianowicz et al., Protonation dynamics of the alpha-toxin ion channel from spectral analysis of pH-dependent current fluctuations. Biophys J. Jul. 1995;69(1):94-105.

Khafizov, Single Molecule Force Spectroscopy Of Single Stranded Dna Binding Protein And Rep Helicase. University of Illinois at Urbana—Champaign Dissertation. 2012.

Kim et al., Liquid-slate field-effect transistors using electrowetting. Applied Physics Letters. 90:043507-1-043507-3.

Korolev et al., Major domain swiveling revealed by the crystal structures of complexes of E. coli Rep helicase bound to single-stranded DNA and ADP. Cell. Aug. 22, 1997;90(4):635-47.

Krantz Lab. Planar Lip Bilayer Electrophysiology Equipment. Department of Molecular & Cell Biology, University of California, Berkeley. Oct. 6, 2007. Last accessed at mcb.berkeley.edu/labs/krantz/equipment/blm.html on Nov. 26, 2014.

Kung et al., Printing via Photolithography on Micropartitioned Fluid Lipid Membranes. Adv. Materials. 2000;12(10):731-734.

Langecker et al., Synthetic lipid membrane channels formed by designed DNA nanostructures. Science. Nov. 16, 2012;338(6109):932-6. doi: 10.1126/science.1225624.

Le Pioufle et al., Lipid bilayer microarray for parallel recording of transmembrane ion currents. Anal Chem. Jan. 1, 2008;80(1):328-32. Epub Nov. 15, 2007.

Lee et al., Ion channel switch array: A biosensor for detecting multiple pathogens. Industrial Biotechnology. May 2005;1(1):26-31. doi:10.1089/ind.2005.1.26.

Lee et al., Nanoarrays of tethered lipid bilayer rafts on poly(vinyl alcohol) hydrogels. Lab Chip. Jan. 7, 2009;9(1):132-9. doi: 10.1039/b809732a. Epub Oct. 22, 2008.

Lee et al., Polyelectrolyte Micropatterning Using Agarose Plane Stamp and a Substrate Having Microscale Features on Its Surface. Bull. Korean Chem. Soc., vol. 26(10):1539-1542 (2005).

Lewis et al., The Mesomorphic Phase Behavior of Lipid Bilayers. Structure Biological Membranes. 3rd Ed. Ed: Yeagle. CRC Press 2011. 19-89.

Li et al., Microfluidic system for planar patch clamp electrode arrays. Nano Lett. Apr. 2006;6(4):815-9.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Luan et al., Base-by-base ratcheting of single stranded DNA through a solid-state nanopore.Phys Rev Lett. Jun. 11, 2010;104(23):238103. Epub Jun. 10, 2010.

Mach et al., Miniaturized planar lipid bilayer: increased stability, low electric noise and fast fluid perfusion. Anal Bioanal Chem. Feb. 2008;390(3):841-6. Epub Oct. 31, 2007.

Majd et al., Hydrogel stamping of arrays of supported lipid bilayers with various lipid compositions for the screening of drug-membrane and protein-membrane interactions. Angew Chem Int Ed Engl. Oct. 21, 2005;44(41):6697-700.

Malmstadt et al., Automated formation of lipid-bilayer membranes in a microfluidic device. Nano Lett. Sep. 2006;6(9):1961-5.

Mangold et al., Reference electrodes based on conducting polymers. Fresenius J Anal Chem. Jun. 2000;367(4):340-2.

Mastrangeli et al., Challenges for Capillary Self-Assembly of Microsystems. IEEE Transactions. Jan. 2011;1(1):133-149.

Mastrangeli et al., Self-assembly from milli- to nanoscales: methods and applications. J Micro Microeng. 2009;19:083001.

Maurer et al., Reconstitution of ion channels in agarose-supported silicon orifices. Biosens Bioelectron. May 15, 2007;22(11):2577-84. Epub Nov. 13, 2006.

McAlduff et al., Freestanding lipid bilayers as substrates for electron cryomicroscopy of integral membrane proteins. J Microsc. Feb. 2002;205(Pt 2):113-7.

Montal et al., Formation of bimolecular membranes from lipid monolayers and a study of their electrical properties. Proc Natl Acad Sci U S A. Dec. 1972;69(12):3561-6.

Moran-Mirabal et al., Micrometer-sized supported lipid bilayer arrays for bacterial toxin binding studies through total internal reflection fluorescence microscopy. Biophys J. Jul. 2005;89(1):296-305. Epub Apr. 15, 2005.

Ogier et al., Suspended Planar Phospholipid Bilayers on Micromachined Supports, Langmuir, vol. 16:5696-5701 (2000).

Onoe et al., Three-Dimensional Micro-Self-Assembly Using Hydrophobic Interaction Controlled by Self-Assembled Monolayers. J Micro Systems. Aug. 2004;13(4):603-611.

Parthasarathy et al., Protein patterns at lipid bilayer junctions. Proc Natl Acad Sci U S A. Aug. 31, 2004; 101(35):12798-803. Epub Aug. 20, 2004.

Peterman et al., "Ion Channels and Lipid Bilayer Membranes Under High Potentials Using Microfabricated Apertures," Biomedical Microdevices, vol. 4(3):231-236 (2002).

Polk et al., Ag/AgC1 microelectrodes with improved stability for microfluidics, Sensors and Actuators B., vol. 114:239-247 (2006).

Rauf et al., Studies on sildenafil citrate (Viagra) interaction with DNA using electrochemical DNA biosensor. Biosens Bioelectron. May 15, 2007;22(11):2471-7. Epub Nov. 7, 2006.

Romer et al., Impedance analysis and single-channel recordings on nano-black lipid membranes based on porous alumina. Biophys J. Feb. 2004;86(2):955-65.

Sackmann, Supported membranes: scientific and practical applications. Science. Jan. 5, 1996;271(5245):43-8.

Sandison et al., "Rapid fabrication of polymer microfluidic systems for the production of artificial lipid bilayers," J. Micromech. Microeng., vol. 15:S139-S144 (2005).

Sandison et al., Air-exposure technique for the formation of artificial lipid bilayers in microsystems. Langmuir. Jul. 17, 2007;23(15):8277-84. Epub Jun. 22, 2007.

(56) References Cited

OTHER PUBLICATIONS

Sapra et al., Lipid-coated hydrogel shapes as components of electrical circuits and mechanical devices. Sci Rep. 2012;2:848. doi: 10.1038/srep00848. Epub Nov. 14, 2012.
Sarles et al., Bilayer formation between lipid-encased hydrogels contained in solid substrates. ACS Appl Mater Interfaces. Dec. 2010;2(12):3654-63. doi: 10.1021/am100826s. Epub Nov. 10, 2010.
Schindler et al., Branched bimolecular lipid membranes. Biophys J. Sep. 1976;16(9):1109-13.
Schmidt et al., A Chip-Based Biosensor for the Functional Analysis of Single Ion Channels. Angew Chem Int Ed Engl. Sep. 1, 2000;39(17):3137-3140.
Shim et al., Stochastic sensing on a modular chip containing a single-ion channel. Anal Chem. Mar. 15, 2007;79(6):2207-13. Epub Feb. 9, 2007.
Smith et al., Micropatterned fluid lipid bilayer arrays created using a continuous flow microspotter. Anal Chem. Nov. 1, 2008;80(21):7980-7. doi: 10.1021/ac800860u. Epub Oct. 8, 2008.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.
Sun et al., Microfluidic static droplet arrays with tuneable gradients in material composition. Lab Chip. Dec. 7, 2011;11(23):3949-52. doi: 10.1039/c11c20709a. Epub Oct. 12, 2011.
Suzuki et al., Highly reproducible method of planar lipid bilayer reconstitution in polymethyl methacrylate microfluidic chip. Langmuir. Feb. 14, 2006;22(4):1937-42.
Suzuki et al., Planar lipid bilayer reconstitution with a micro-fluidic system. Lab Chip. Oct. 2004;4(5):502-5. Epub Sep. 2, 2004.
Suzuki et al., Planar Lipid Membrane Array for Membrane Protein Chip. 17th IEEE International Conference on Micro Electro Mechanical Systems (MEMS), pp. 272-275 (2004).
Syms et al., Surface Tension-Powered Self-Assembly of Microstructures—The State of the Art. J Micro Systems. Aug. 2003;12(4):387-417.
Thorsen et al., Dynamic pattern formation in a vesicle-generating microfluidic device. Phys Rev Lett. Apr. 30, 2001;86(18):4163-6.
Urisu et al., Formation of high-resistance supported lipid bilayer on the surface of a silicon substrate with microelectrodes. Nanomedicine. Dec. 2005;1(4):317-22.
Vidinha et al., Ion jelly: a tailor-made conducting material for smart electrochemical devices. Chem Commun (Camb). Nov. 30, 2008;(44):5842-4. doi: 10.1039/b811647d. Epub Oct. 3, 2008.
Vulto et al., Microfluidic channel fabrication in dry film resist for production and prototyping of hybrid chips. Lab Chip. Feb. 2005;5(2):158-62. Epub Dec. 3, 2004.
Wagterveld et al., Ultralow hysteresis superhydrophobic surfaces by excimer laser modification of SU-8. Langmuir. Dec. 19, 2006;22(26):10904-8.
Watanabe et al., Electrical recording of Nanopore membrane proteins in a microfluidic device. The Papers of Technical Meeting on Bio Micro Systems, IEE Japa. 2010; BMS-10(7-27):5-8.
Yusko et al., Controlling protein translocation through nanopores with bio-inspired fluid walls. Nat Nanotechnol. Apr. 2011; 6(4): 253-260. Epub Feb. 20, 2011. doi: 10.1038/nnano.2011.12.
Zagnoni et al., Bilayer lipid membranes from falling droplets. Anal Bioanal Chem. Mar. 2009;393(6-7):1601-5. doi:10.1007/s00216-008-2588-5. Epub Jan. 19, 2009.
Zagnoni et al., Controlled delivery of proteins into bilayer lipid membranes on chip. Lab Chip. Sep. 2007;7(9):1176-83. Epub Jun. 27, 2007.
Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.
Third Party Observations for EP 17739663.7, mailed Sep. 23, 2021. 18 pages.
PCT/GB2013/050333, Aug. 19, 2013, International Search Report and Written Opinion.
PCT/GB2013/050333, Aug. 19, 2014, International Preliminary Report on Patentability.

* cited by examiner

Fig. 11b
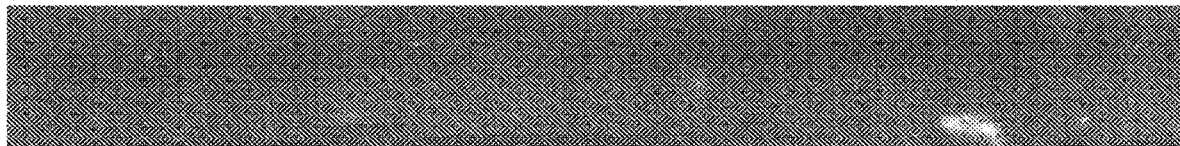
Fig. 11a     Fig. 11c     Fig. 11e
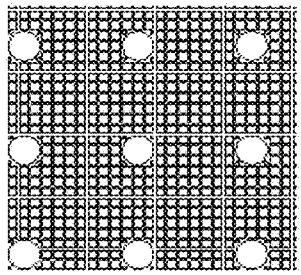 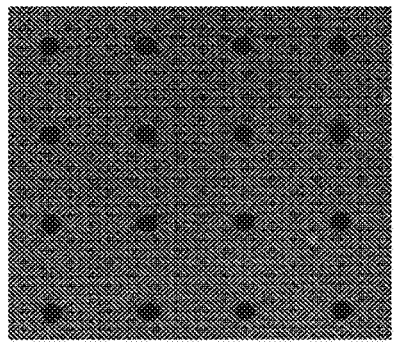 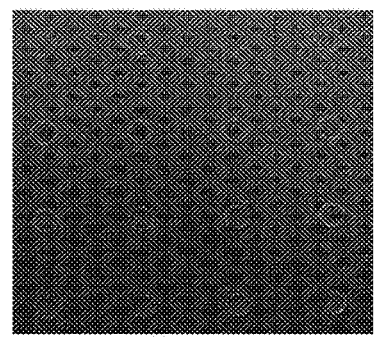
Fig. 11d
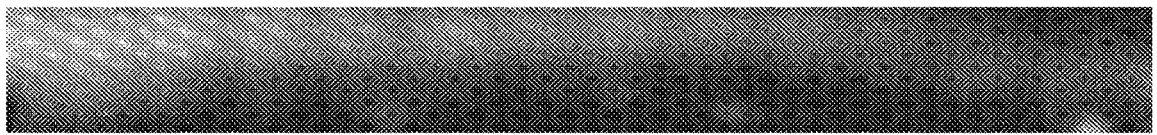

APPARATUS FOR SUPPORTING AN ARRAY OF LAYERS OF AMPHIPHILIC MOLECULES AND METHOD OF FORMING AN ARRAY OF LAYERS OF AMPHIPHILIC MOLECULES

RELATED APPLICATIONS

This application is a continuation of U.S. application Ser. No. 14/378,557, filed Aug. 13, 2014, which is a 35 U.S.C. § 371 national stage filing of International Application PCT/GB2013/050333, filed Feb. 13, 2013, which claims priority to Great Britain Application No. 1202519.3 filed on Feb. 13, 2012, the entire contents of each of which applications are incorporated herein by reference for all purposes.

FIELD

The present invention relates to an apparatus for supporting an array of amphiphilic molecules and a method of forming such an array. In particular, the invention relates to the efficient formation of arrays of amphiphilic molecules. One area of application is the preparation of lipid bilayers.

BACKGROUND

In one type of known technique, a membrane based layer of amphiphilic molecules may be used as a means of separating two volumes of aqueous solution. The amphiphilic layer resists the flow of current between the volumes when a potential difference is applied between the two volumes. A membrane penetrating protein is inserted into the amphiphilic layer to allow the passage of ions across the layer, which is recorded as an electrical signal detected by electrodes placed in each of the aqueous solutions, such as disclosed in WO2009/077734.

In this technique, a target analyte may interact with the membrane penetrating protein to modulate the flow of ions and may be detected by observing the resultant variations in the electrical signal. This technique therefore allows the layer of amphiphilic molecules to be used as a biosensor to detect the analyte.

The layer of amphiphilic molecules has a two-fold purpose in this technique. Firstly, the layer provides a platform for the protein that acts as a sensing element. Secondly, the layer isolates the flow of ions between the volumes. The electrical resistance of the layer ensures that the dominant contribution of ionic flow in the system is through the membrane protein of interest, with negligible flow through the layer of amphiphilic molecules, thus allowing detection with single protein channels.

A specific application of this technique is in nanopore sensing, where the number of membrane proteins is kept small, typically between 1 and 100, so that the behaviour of a single protein molecule can be monitored electrically. This method gives information on each specific molecular interaction and hence provides richer information than a bulk measurement. However, due to the small currents involved, typically a few pA, this approach relies on the formation of a very high resistance seal, typically greater than 1 GΩ, and sufficient electrical sensitivity to measure the current.

While the requirements for stochastic sensing have been met in the laboratory, conditions and expertise limit its practical application in commercial products. In addition, laboratory methods are laborious and time-consuming and are not scalable easily to the high-density arrays that are desirable for any commercial biosensor. Furthermore, the fragility of single amphiphilic layer membranes means that they can be difficult to form, so that anti-vibration tables are often employed in the laboratory. Necessitating the use of such anti-vibration tables would not be desirable in a commercial product.

There have been great efforts to increase the ease of bilayer formation using micro fabrication. Some techniques have attempted to miniaturise standard systems for folded lipid bilayers or painted lipid bilayers. Other techniques include bilayer formation on solid substrates or directly on electrode surfaces, through either absorption or adsorption. A large proportion of nanopore sensing devices form a bilayer by using a variant of either the folded lipid bilayers technique, or the painted bilayer technique. To date, most have concentrated either on novel methods of aperture formation, on utilising the emerging technologies in micro fabrication to miniaturise the device, or to create a plurality of addressable sensors such as disclosed in EP2107040 and WO2010/122293.

There are problems associated with the conventional supported amphiphilic layer approach that makes the approach unsuitable. The first problem lies with the resistance of the lamellar membrane which typically is about 100MΩ. While this may be suitable for examining protein behaviour at large protein concentrations, it is not sufficient for a high-fidelity assay based on single molecule sensing. To achieve single-molecule sensing a resistance of at least 1 GΩ, and for some applications one or two orders of magnitude higher, is required. The second problem relates to the small volume of solution trapped in the small distance between the amphiphilic layer and the solid support, typically of the order of 1 nm. This small volume does not contain many ions, and this affects the stability of the potential across the amphiphilic layer and limits the duration for which recording can be performed.

The techniques used in the silicon chip industry provide an attractive technology for creating a large number of electrodes that could be used in biosensor applications. This approach is disclosed in the related applications U.S. Pat. Nos. 7,144,486 and 7,169,272. 7,144,486 discloses a method of fabricating a microelectrode device containing microcavities etched into layers of an insulator material. The devices are said to have a wide range of electrochemical applications in which electrodes in the cavities allow measurement of electrical signals.

In summary, the known technologies discussed above either present methods of amphiphilic layer formation that cannot reproducibly achieve high resistances; suffer from low ionic reservoirs; are not capable of high duration direct current measurements; and/or require a separate fluidic chamber for each array element. This limits the scale up of the techniques to produce a high-density array device.

WO 2009/077734 describes a simplified apparatus to prepare amphiphilic layers across a recess and to scale the apparatus with multiple recesses forming chambers of a large scale sensor array without any need for a complicated apparatus.

In this method a lipid amphiphilic layer is formed as a layer separating two volumes of aqueous solution, the method comprising: (a) providing an apparatus comprising elements defining a chamber, the elements including a body of non-conductive material having formed therein at least one recess opening into the chamber, the recess containing an electrode; (b) applying a pre-treatment coating of a hydrophobic fluid to the body across the recess; (c) flowing aqueous solution, having amphiphilic molecules added thereto, across the body to cover the recess so that aqueous solution is introduced into the recess from the chamber and so that a layer of the amphiphilic molecules forms across the recess separating a volume of aqueous solution A key feature of this method is the preparation of high quality amphiphilic layers that are suitable for high sensitivity biosensor applications such as nanopore sensing and single channel recording. The method has been demonstrated to form amphiphilic layers of high resistance, providing highly resistive electrical seals having an electrical resistance of greater than 1 GΩ, typically 100 GΩ, which for example, enable high-fidelity recordings from single protein pores.

In this method, formation of a layer of the amphiphilic molecules across a recess simply by flowing the aqueous solution across the body to cover the recess is possible provided that a pre-treatment coating of a hydrophobic fluid is applied to the body across the recess. The pre-treatment coating assists formation of the amphiphilic layer and aids the wetting of the microcavity, forming the sensor well, with aqueous solution.

However, under some circumstances the formation of high quality amphiphilic layers may be compromised. The present invention aims to at least partly address this problem.

SUMMARY

According to a first aspect of the invention there is provided an apparatus for supporting an array of layers of amphiphilic molecules, the apparatus comprising: a body, formed in a surface of the body, an array of sensor wells capable of supporting a layer of amphiphilic molecules across the sensor wells, the sensor wells each containing an electrode for connection to an electrical circuit, and formed in the surface of the body between the sensor wells, flow control wells capable of smoothing the flow of a fluid across the surface.

This aspect is directed to a body in which inactive flow control wells are provided for increasing uniformity of distribution. That is, the additional wells reduce any stick/slip characteristics, resulting in a more predictably uniform wetted surface. The provision of the additional wells allows the sensor wells to be distributed and function as desired, without needing to account for the wetting characteristics of the system. That is, the desired sensor well distribution can be selected, and the additional wells can be supplied to account for the system wetting characteristics.

Optionally, the cross-sectional area of a flow control well is less than the area of a sensor well.

Optionally, the flow control wells do not contain electrodes. Alternatively, the flow control wells each contain an electrode, the electrodes in the sensor wells being connected to the electrical circuit but the electrodes in the flow control wells not being connected to the electrical circuit. In the embodiments where the flow control wells do not function as active sensor wells, their function is to solely improve the wetting characteristics of the system. As such the constraint of requiring the flow control wells to be able to function as flow sensor wells is removed and the flow control wells may be provided of dimensions, for example the cross-sectional area of the aperture or shape of the wells, or of a pitch that are/is unsuitable for use as sensor wells.

Optionally, the apparatus further comprises a cover over the surface of the body defining a cavity therebetween, and a common electrode arranged in the cavity for connection to the electrical circuit. The cover can have an internal surface facing the surface of the body that is roughened to smooth the flow of fluid thereover.

Optionally, the array of sensor wells is a regular array, and the flow control wells consist of a regular array of flow control wells. Optionally, the pitch of the array of at least a portion of the flow control wells is smaller than the pitch of at least a portion of the array of sensor wells. That is, the axial distance between the flow control wells can be smaller than the axial distance between the sensor wells. The flow control wells may be of a different dimension than the flow sensor wells, for example a different size, a different cross-sectional area and/or a different cross-sectional area of the aperture than the sensor wells. Optionally, the sensor wells are circular, and optionally the flow control wells are square. Optionally, the flow control wells are distributed over a larger area than the sensor wells.

Optionally, the sensor wells and flow control wells are arranged such that a pre-treatment, being a fluid capable of interacting with the amphiphilic molecules, on the surface would not enter the Cassie-Baxter state. Optionally, the sensor wells and flow control wells are shaped to provide a surface roughness r, defined as the total area of the surface and wells divided by the projected area of the surface, and a solid surface area fraction f, defined as the area of the surface between the wells divided by the projected area of the surface, that meet the requirement in respect of a pre-treatment, that is a fluid capable of interacting with the amphiphilic molecules, having a contact angle θ that $((\varphi-1)/(r-\varphi))>\cos(\theta)$. This ensures that the pre-treatment can enter the wells.

Optionally, the wells are formed on the surface with a number density of $3.2\times10^{-5}$ wells/micron$^2$ or more, optionally $6.4\times10^{-5}$ wells/micron$^2$ or more, further optionally $1.5\times10^{-4}$ wells/micron$^2$ or more, and still further optionally $2.5\times10^{-4}$ wells/micron$^2$ or more.

Optionally, the apparatus further comprises a pre-treatment of a hydrophobic fluid applied to the surface of the body.

According to this aspect, there is also provided a method of preparing an apparatus for forming an array of amphiphilic layers, the method comprising: providing an apparatus as discussed above; delivering across the surface of the body to the wells a pre-treatment coating of a hydrophobic fluid. The pre-treatment coating serves to support the amphiphilic layer such that a highly resistive electrical seal may be formed across the well.

Optionally, the pre-treatment is delivered in a solvent, the method further comprising drying the surface of the body to remove the solvent. Said step of drying the surface of the body to remove the solvent is preferably performed under a pressure below atmospheric pressure.

Optionally, the method is performed so that each of the following conditions is met: the visible coverage of the surface by the pre-treatment is less than 15% of the area in which the array of sensor wells is located; the proportion of sensor wells that are filled is less than 5%; and the values of rectangularity and the perimeter of all the annuli of pre-treatment around the respective sensor wells falls within a 40% of the average values. Further optionally, the method is performed so that each of the following conditions is met: the visible coverage of the surface by the pre-treatment is less than 5% of the area in which the array of sensor wells is located; the proportion of sensor wells that are filled is less than 0.5%; and the values of rectangularity and the perimeter of all the annuli of pre-treatment around the respective sensor wells falls within a 20% of the average values. In this context, the 'average values' refer to the mean values of the rectangularity and the perimeter of the annuli, respectively, as calculated for all the sensor wells.

According to this aspect, there is also provided a method of forming an array of the sensor wells each containing an electrode for connection to an electrical circuit, wherein the wells have a number density of $3.2 \times 10^{-5}$ wells/micron$^2$ or more, optionally $6.4 \times 10^{-5}$ wells/micron$^2$ or more, further optionally $1.5 \times 10^{-4}$ wells/micron$^2$ or more, and still further optionally $2.5 \times 10^{-4}$ wells/micron$^2$ or more.

Optionally, all the wells are sensor wells. Alternatively, some of the wells are sensor wells, and the remainder of the wells are flow control wells, formed in the surface of the body between the sensor wells.

Optionally, the area of a flow control well is less than the area of a sensor well.

Optionally, the flow control wells do not contain electrodes. Alternatively, the flow control wells each contain an electrode, the electrodes in the sensor wells being connected to the electrical circuit but the electrodes in the flow control wells not being connected to the electrical circuit.

Optionally, the array of sensor wells is a regular array, and the flow control wells consist of a regular array of flow control wells. Optionally, a pitch of the array of flow control wells is smaller than a pitch of the array of sensor wells. Optionally, the sensor wells are circular, and the flow control wells are square.

Optionally, the flow control wells are distributed over a larger area than the sensor wells.

Optionally, the apparatus further comprises a cover over the surface of the body defining a cavity therebetween, and a common electrode arranged in the cavity for connection to the electrical circuit. Optionally, the cover has an internal surface facing the surface of the body that is roughened to smooth the flow of fluid thereover.

Optionally, the wells have an area density of 0.141 or more.

Optionally, the wells are arranged such that a pre-treatment applied to the surface of the body does not enter the Cassie-Baxter state. Optionally, the sensor wells and flow control wells are shaped to provide a surface roughness r, defined as the total area of the surface and wells divided by the projected area of the surface, and a solid surface area fraction f, defined as the area of the surface between the wells divided by the projected area of the surface, that meet the requirement in respect of a pre-treatment, that is a fluid capable of interacting with the amphiphilic molecules, having a contact angle $\theta$ that $((\varphi-1)/(r-\varphi))>\cos(\theta)$.

Optionally, the apparatus further comprises a pre-treatment of a hydrophobic fluid that is applied to the sensor wells.

According to the second aspect, there is also provided a method of preparing an apparatus for forming an array of sensor wells, the method comprising: providing an apparatus of the second aspect, as discussed above; delivering across the surface of the body to the wells a pre-treatment of a hydrophobic fluid.

Optionally, the pre-treatment is delivered in a solvent, the method further comprising drying the surface of the body to remove the solvent. Optionally, the step of drying the surface of the body to remove the solvent is performed under a pressure below atmospheric pressure.

Optionally, the method is performed so that each of the following conditions is met: the visible coverage of the surface by the pre-treatment is less than 15% of the area in which the array of sensor wells is located; the proportion of sensor wells that are filled is less than 5%; and the values of rectangularity and the perimeter of all the annuli of pre-treatment around the respective sensor wells falls within a 40% of the average values. Further optionally, the method is performed so that each of the following conditions is met: the visible coverage of the surface by the pre-treatment is less than 5% of the area in which the array of sensor wells is located; the proportion of sensor wells that are filled is less than 0.5%; and the values of rectangularity and the perimeter of all the annuli of pre-treatment around the respective sensor wells falls within a 20% of the average values.

According to the second aspect, there is also provided a method of forming an array of layers of amphiphilic molecules, the method comprising: preparing an apparatus by a method of the second aspect, as discussed above; and flowing a fluid containing amphiphilic molecules across the surface of the body to form layers of amphiphilic molecules across at least some of the array of sensor wells.

According to a third aspect, there is provided a method of preparing an apparatus for forming an array of layers of amphiphilic molecules, the method comprising: providing an apparatus comprising a body, and, formed in a surface of the body, an array of wells, at least some of which are sensor wells capable of supporting a layer of amphiphilic molecules across the sensor wells after application to the sensor wells of a pre-treatment of a hydrophobic fluid, the sensor wells each containing an electrode for connection to an electrical circuit, and delivering across the surface of the body a pre-treatment, that is a fluid capable of interacting with the amphiphilic molecules, in a solvent to apply the pre-treatment to the wells; and drying the surface of the body to remove the solvent under a pressure below atmospheric pressure.

According to this aspect, the use of low-pressure drying produces a more uniform dried pre-treatment on the surface of the body.

Optionally, the apparatus is an apparatus according to the first or second aspect, discussed above.

Optionally, the method can be performed so that each of the following conditions is met: the visible coverage of the surface by the pre-treatment is less than 15% of the area in which the array of sensor wells is located; the proportion of sensor wells that are filled is less than 5%; and the values of rectangularity and the perimeter of all the annuli of pre-treatment around the respective sensor wells falls within a 40% of the average values. Further optionally, the method can be performed so that each of the following conditions is met: the visible coverage of the surface by the pre-treatment is less than 5% of the area in which the array of sensor wells is located; the proportion of sensor wells that are filled is less than 0.5%; and the values of rectangularity and the perimeter of all the annuli of pre-treatment around the respective sensor wells falls within a 20% of the average values.

The third aspect of the invention also provides a method of forming an array of layers of amphiphilic molecules, the method comprising: preparing an apparatus by a method according to the method of the third aspect, as discussed above; and flowing a fluid containing amphiphilic molecules across the surface of the body to form layers of amphiphilic molecules across at least some of the array of sensor wells.

According to a fourth aspect of the invention, there is provided a method of preparing an apparatus for forming an array of layers of amphiphilic molecules, the method comprising: providing an apparatus comprising a body, and, formed in a surface of the body, an array of wells, at least some of which are sensor wells capable of supporting a layer of amphiphilic molecules across the sensor wells after application to the sensor wells of a pre-treatment of a hydrophobic fluid, the sensor wells each containing an electrode for connection to an electrical circuit, and delivering to the body a pre-treatment of a hydrophobic fluid, the method being performed so that each of the following conditions is met: the visible coverage of the surface by the pre-treatment is less than 15% of the area in which the array of sensor wells is located; the proportion of sensor wells that are filled is less than 5%; and the values of rectangularity and of the perimeter of each of the annuli of pre-treatment around the respective sensor wells falls within 40% of the average values. The visible coverage can be determined with any appropriate light-source. For example, under appropriate lighting conditions, the coverage may be visible in normal light. Alternatively, additives in the pre-treatment may be used to highlight the coverage under particular lighting conditions. For example, in one embodiment of the invention, a green fluorescent dye (a boron-dipyrromethene) is used to highlight the pre-treatment and a red fluorescent dye (sulforhodamine) is used to highlight the buffer under the membrane layer.

Optionally, the method is performed so that each of the following conditions is met: the visible coverage of the surface by the pre-treatment is less than 5% of the area in which the array of sensor wells is located; the proportion of sensor wells that are filled is less than 0.5%; and the values of rectangularity and the perimeter of all the annuli of pre-treatment around the respective sensor wells falls within a 20% of the average values.

Optionally, the pre-treatment is applied to the body in a solvent, and the method further comprises drying the surface of the body to remove the solvent, the method being performed so that said conditions are met after said drying.

The fourth aspect further provides a method of forming an array of layers of amphiphilic molecules, the method comprising: preparing an apparatus according to the method of the fourth aspect, discussed above; and flowing a fluid containing amphiphilic molecules across the surface of the body to form layers of amphiphilic molecules across at least some of the array of sensor wells.

The fourth aspect further provides an apparatus for forming an array of layers of amphiphilic molecules, the apparatus comprising: a body; and formed in a surface of the body, an array of wells, at least some of which are sensor wells capable of supporting a layer of amphiphilic molecules across the sensor wells after application to the sensor wells of a pre-treatment of a hydrophobic fluid, the sensor wells each containing an electrode for connection to an electrical circuit, the array of wells being arranged such that after delivery to the body of a pre-treatment that is a fluid capable of interacting with the amphiphilic molecules, each of the following conditions is met: the visible coverage of the surface by the pre-treatment is less than 15% of the area in which the array of sensor wells is located; the proportion of sensor wells that are filled is less than 5%; and the values of rectangularity and the perimeter of all the annuli of pre-treatment around the respective sensor wells falls within a 40% of the average values.

Optionally, the array of wells is arranged such that after delivery to the body of a pre-treatment of a hydrophobic fluid, each of the following conditions is met: the visible coverage of the surface by the pre-treatment is less than 5% of the area in which the array of sensor wells is located; the proportion of sensor wells that are filled is less than 0.5%; and the values of rectangularity and the perimeter of all the annuli of pre-treatment around the respective sensor wells falls within a 20% of the average values.

Optionally, the apparatus further comprises a pre-treatment of a hydrophobic fluid applied to the sensor wells.

BRIEF DESCRIPTION OF THE DRAWINGS

The present invention will be described with reference to exemplary embodiments and the accompanying Figures in which:

FIG. 11a is a schematic representation of a fifth design,
and FIGS. 11b-11e are images showing pre-treatment dispersal for the fifth design.

DETAILED DESCRIPTION

As mentioned above, the techniques of WO 2009/077734, herein incorporated by reference in its entirety, can result in amphiphilic layers of compromised quality in some circumstances. The present invention has identified that this can be the result of the pre-treatment coating being, in some parts of the array, either greater or less than an optimal level.

Figure 1:
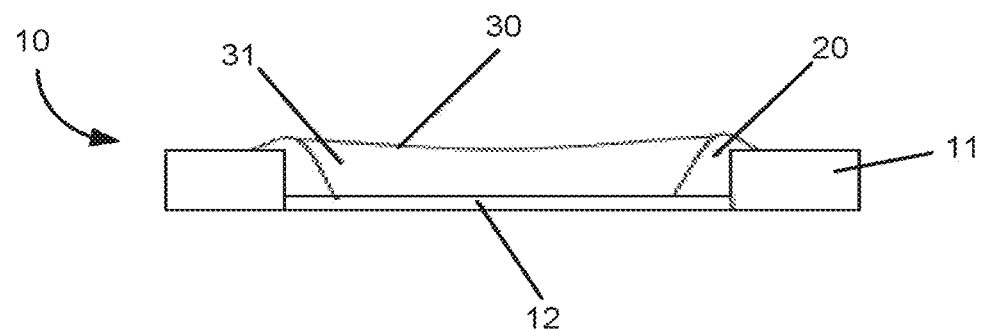
FIG. 1 is a diagram of ideal fluid behaviour in a well.

FIG. 1 shows a schematic cross section through a microcavity or sensor well 10 of a sensor array. The well 10 is formed in a material 11 such as SU-8 forming a body, and many wells 10 may be formed in close proximity within the material to form an array of sensor wells. Preferably the material in which the wells are formed is itself solid and not porous, so that the wells maintain their integrity and liquid does not leak or leach from the wells. The body may also be made of other materials such as such as a positive or negative photoresists, plastics such as polycarbonate or polyester or solid state inorganic materials such as silicon, glass or silicon nitride. Examples of photoresists that may be used are SU8 2000 or 3000 series materials, poly(methyl methacrylate) (PMMA), poly(methyl glutarimide) (PMGI), phenol formaldehyde resin (DNQ/Novolac), or polyhydroxystyrene-based polymers. At the bottom of the well is an electrode 12 for connection to an electrical circuit, which can be used (in combination with another electrode above the well, not shown in FIG. 1) to monitor the flow of current through the well 10.

In practice, an array of such sensor wells 10 formed in a body will be provided in an apparatus further comprising a cover over the surface of the body, so as to define a cavity between the cover and the body. An electrode is arranged in the cavity for connection to the electrical circuit, and acts a common electrode for the wells in the array.

FIG. 1 shows the ideal configuration, in which a pre-treatment 20 is pinned tightly to the edges of the well 10. This configuration allows for the maximum trapped volume (i.e. volume of amphiphilic layer 30) within the well 10. This configuration results in a biosensor with the longest lifetime.

The pre-treatment is a fluid capable of interacting with the amphiphilic molecules. The pre-treatment coating is typically a hydrophobic substance, usually having long chain molecules, in an organic solvent. Suitable organic substances include without limitation: n-decane, hexadecane, isoecoisane, squalene, pristane (2,6,10,14-tetramethylpentadecane), fluorinated oils (suitable for use with fluorinated lipids), alkyl-silane (suitable for use with a glass membrane) and alkyl-thiols (suitable for use with a metallic membrane). Suitable solvents include but are not limited to: pentane, hexane, heptane, octane, decane, and toluene. The material might typically be 0.1 µl to 10 µl of 0.1% to 50% (v/v) hexadecane in pentane or another solvent, for example 2 µl of 1% (v/v) hexadecane in pentane or another solvent, in which case lipid, such as diphantytanoyl-sn-glycero-3-phosphocholine (DPhPC), might be included at a concentration of 0.6 mg/ml.

Some specific materials for the pre-treatment coating 30 are set out in Table 1 by way of example and without limitation.

TABLE 1

Examples of pre-treatment materials.

| Pre-treatment formulation | Volumes applied |
| --- | --- |
| 0.3% hexadecane in pentane | 2 × 1 µl |
| 1% hexadecane in pentane | 2 × 2 × 0.5 µl; 2 × 0.5 µl; 1 µl; 2 × 1 µl; 2 × 1 µl; 2 µl; 2 × 2 µl; 5 µl |
| 3% hexadecane in pentane | 2 × 1 µl; 2 µl |
| 10% hexadecane in pentane | 2 × 1 µl; 2 µl; 5 µl |
| 0.5% hexadecane + 0.6 mg/ml DPhPC lipid in pentane | 5 µl |
| 1.0% hexadecane + 0.6 mg/ml DPhPC lipid in pentane | 2 × 2 × 0.5 µl |
| 1.5% hexadecane + 0.6 mg/ml DPhPC lipid in pentane | 2 µl; 2 × 1 µl |

The amphiphilic layer can be made of any amphiphile that forms a lamellar phase. Amphiphiles include lipids capable of forming lipid bilayers. The amphiphiles are chosen such that an amphiphilic layer having the required properties, such as surface charge, ability to support membrane proteins, packing density or mechanical properties, is formed. The amphiphiles can comprise one or more different components. For instance, the amphiphiles can contain up to 100 amphiphiles. The amphiphiles may be naturally-occurring or synthetic. The amphiphile may be a block copolymer.

In embodiments where the amphiphile is a lipid, the lipid typically comprises a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS); phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

The lipid can also be chemically-modified. The head group or the tail group of the lipid may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerizable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine.

The lipid may comprise one or more additives that will affect the properties of the lipid bilayer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides. The lipid preferably comprises cholesterol and/or ergosterol when membrane proteins are to be inserted into the amphiphilic layer.

Figure 2:
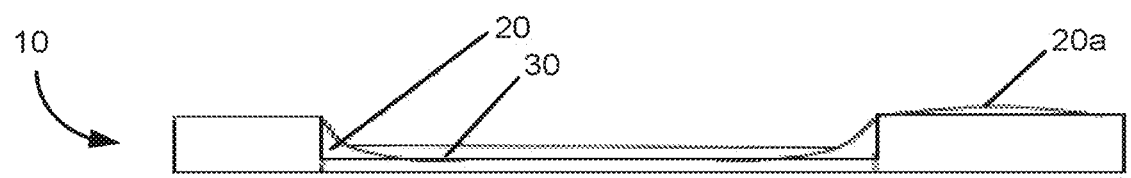
FIG. 2 is a diagram of undesirable fluid behaviour in a well.

When pre-treatment oil 20 is not deposited in the optimum configuration of FIG. 1, a smaller trapped volume is the most probable outcome. There is also a higher probability that excess pre-treatment oil will be located on the upper surface of the well 10. This is shown schematically in FIG. 2. In FIG. 2, the pre-treatment 20 is not pinned tightly to the edges of the well 10. As a result, the trapped volume of the amphiphilic molecule 30 is reduced. Further, pre-treatment 20a is also present on the upper surface of the well 10.

In order to form a good contact between pre-treatment 20 and the amphiphilic layer 30, it is preferable to use a hydrophobic material for forming the well 10. This encourages a small contact angle between the pre-treatment 20 and the amphiphilic layer 30. However, this also makes it more likely that pre-treatment oil will form droplets 20a on the surface of the array material unless pinned into the well 10 and collected by Laplace pressures. The appropriate hydrophobic surface properties may be achieved by suitable selection of materials. However, where there are conflicting constraints, for example where the desired surface properties are not available using photoresist material appropriate for fabrication of the required structure, this may not be possible. In this case, commonly, surface treatments are applied to achieve a hydrophilic surface, such as the addition of a chemical coating or plasma modification. These methods are not ideal, typically they are unstable over a long product storage lifetime or may cause interference with the sensor chemical system.

Where there is a desire to form the amphiphilic layers quickly, requiring fast flow rates over the surface or where a very large scale array is used, it has been found that the flow of aqueous solution during the amphiphilic layer formation phase may cause a transfer of pre-treatment 20 to the downstream areas of the array or lead to the creation of an emulsion in the aqueous solution, which is undesirable. This is more likely in situations where pre-treatment oil 20 is located outside of the well, for example on the SU-8 surface.

In the current invention, the introduction of surface patterning to the bulk surface of the array allows for improved formation of the pre-treatment layer 20 with good uniformity and aids retention of the pre-treatment layer during the subsequent fluid flow associated with amphiphilic layer formation.

The uniformity of pre-treatment distribution can be further enhanced by extending the surface patterning beyond the bulk surface of the array to consider the other internal faces of the fluidic flow cell in which the array is contained. In this example, during the pre-treatment application phase, the pre-treatment oil material is also coated onto all other internal surfaces.

During the subsequent fluid flow steps this material may also be redistributed, therefore compromising formation of high quality lipid amphiphilic layers. A surface pattern can be introduced to these other surfaces, and tailored to control the degree of coating with pre-treatment and to enhance retention of the pre-treatment on those surfaces enhancing the overall performance of the apparatus.

The surface patterning also enables the required surface hydrophobicity, which is conventionally achieved by surface chemistry modification of the array material, to be achieved through altering the ratio of contribution of surface energies between that of the native material and that of air, or whatever the surrounding bulk medium may be.

The surface states that may exist for a well-containing surface are defined by the overall thermodynamic position.

In the 'Cassie-Baxter' state, the hydrophobicity is high enough that the wells are not filled by the wetting fluid, but remain filled with the bulk medium. However, this state is thermodynamically unstable and can, under the correct circumstances, collapse to a lower energy state.

In the most thermodynamically stable 'Wenzel' state, the wells are completely filled by the wetting fluid. Once achieved it is impossible to revert between the Wenzel and Cassie-Baxter states.

Figure 3:
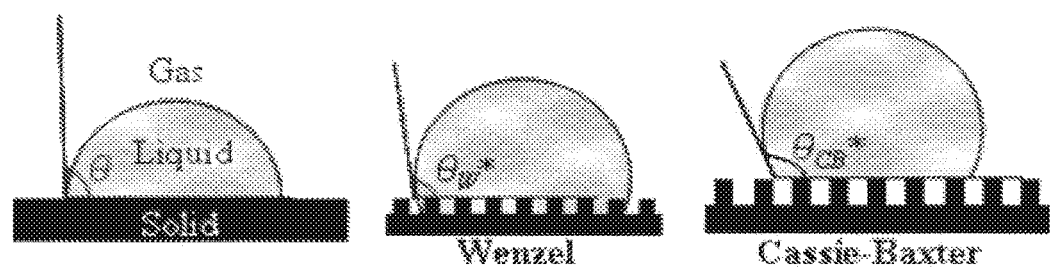
FIG. 3 is a diagram showing different wetting behaviours.

FIG. 3 illustrates the wetting of (a) a flat surface in comparison to wetting a surface containing microstructures in the (b) Wenzel and (c) Cassie-Baxter states. As can be seen from the Figure, the contact angle θ differs in the different states.

The modified angles of the Wenzel, $\theta_W$, and Cassie-Baxter, $\theta_{CB}$, states can be calculated once the contact angle, θ, of the native material is known.

$$\cos\theta_{CB} = \varphi(\cos\theta + 1) - 1$$

$$\cos\theta_W = r\cos\theta$$

where φ is defined as the area of the surface between the wells divided by the projected area of the surface (calculated as: (total area−well area)/(total area)), r is defined as the ratio of true area of the solid surface to the apparent area.

As such it is possible to calculate the effects for both phenomena over a range of fluid contact angles.

Figure 4A:
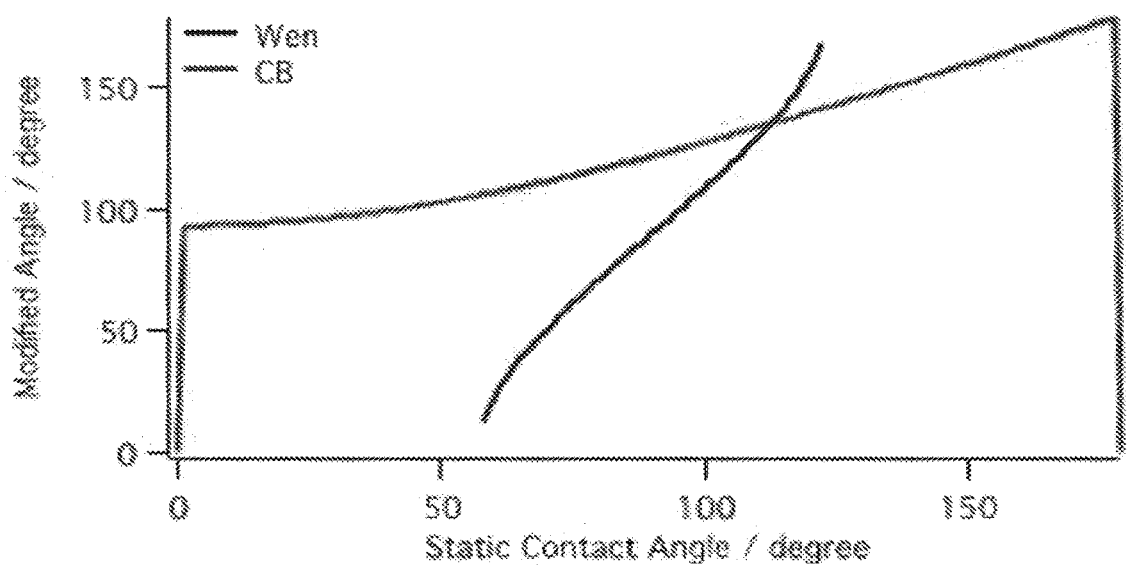
FIGS. 4a and 4b are of the expected modified contact angles for different 'native' contact angles, for an array of 50 micron wells spaced (a) 63 microns apart and (b) 81 microns apart.
Figure 4B:
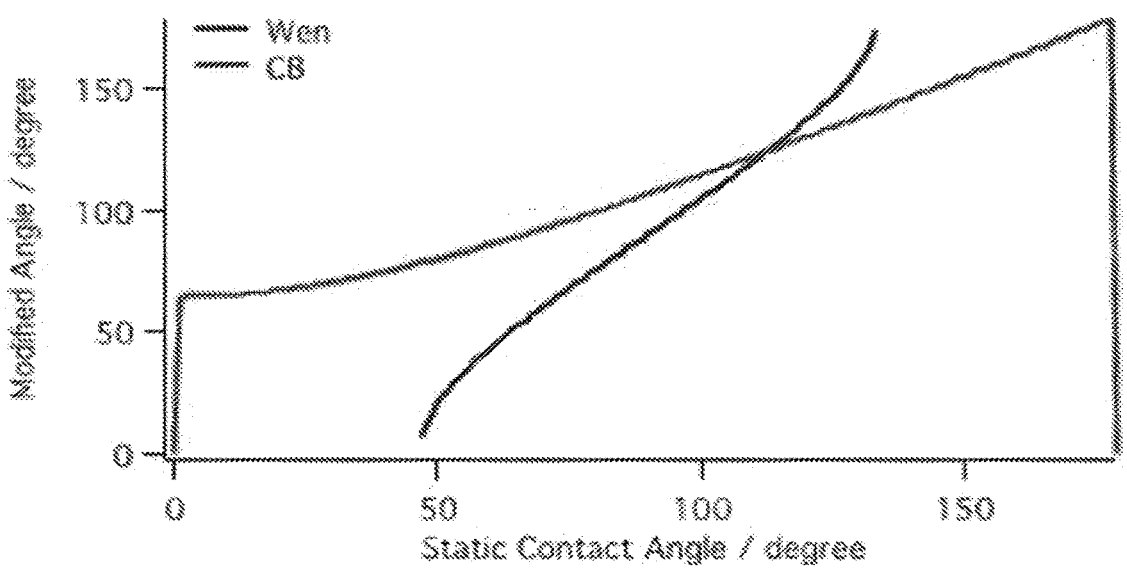

FIGS. 4a and 4b show graphs of the expected modified contact angles for different 'native' contact angles, for an array of 50 micron wells spaced (a) 63 microns apart and (b) 81 microns apart. These graphs show that there is a significant difference in Cassie-Baxter contact angles between surfaces of 50 μm micro-wells spaced either 63 or 81 μm apart. For example, native SU-8 has a contact angle of around 76°, thus, for 63 μm wells, a Wenzel state would have a modified contact angle of around 65°, whilst the Cassie-Baxter state exhibits modified contact angles in the region of 115°.

As such the surface properties of the array can thus be tailored to specific fluids or to produce a desired surface state, by controlling the surface patterning. In particular, it may be desirable to form the array with additional wells, not intended for sensing, in order to modify the surface properties. Such additional wells may be inactive for sensing, either because they do not contain an electrode or because the electrode is not connected to the sensing circuitry. This approach holds several advantages.

For flow through pre-treatment application on the large-scale, the surface can be controlled to promote pinning of the pre-treatment on the sensor array surface so that pre-treatment does not move during amphiphilic layer formation. Additionally, it is preferable to avoid the Cassie-Baxter state, otherwise the pre-treatment will not fill the wells. That is, it is preferable to design the surface to have a contact angle θ for which: $((\varphi-1)/(r-\varphi)) > \cos(\theta)$.

Using a high density of wells, including inactive wells, over the bulk surface forming the surface pattern also allows maximum flexibility into the design. That is, if it becomes desirable to change the arrangement of the sensing wells, for example to produce a more closely packed electronic array, this can be produced with minimal impact to the overall surface by appropriate 'balancing' with inactive wells. That is, the inactive wells can be formed in the surface of the body in which the 'active' wells have been formed, adding to the array of active wells to create the desired surface properties. As a result, the surface properties can remain virtually unaltered whilst varying the structure of the active array, and so the optimal fluidic procedure will not need to be changed. The additional 'flow control' wells may not contain electrodes, or may contain electrodes that are not attached to the electrical circuit of the sensor wells.

Controlling the hydrophobicity based on the well geometry and placement avoids the need for additional processing steps associated with modifying the surface properties by chemical means. Further, this method of surface control is applicable to all materials, making it unnecessary to tailor a particular chemistry to a particular material.

In addition, it has been found that the flow through of pre-treatment is also enhanced by using micro-patterned surfaces. The pre-treatment front can be observed to progress across an array more smoothly in the presence of additional wells, particularly on larger arrays. That is, the additional wells increase the homogeneity of flow across the surface of the body such that the uniformity of wetting is increased. The additional wells are capable of increasing the uniformity of the distribution of said pre-treatment during deliver across the surface of the body. This smoothing reduces the tendency for the fluid to undergo large scale pinning during flow which results in so-called 'stick/slip' movement of a fluid front. Wetting in this stick/slip fashion is irregular and can result in the fluid being pinned for a period of time before moving to the next pinning position. This can also result in de-wetting of surfaces that have already been wetted as the shape of the wetting profile changes. To this end, it can also be preferable to roughen the internal surface of the cover, opposite the body, to further smooth the flow of fluid. It can also be preferable to provide the additional wells over a large area than the sensor wells, in order to ensure the edges of the array of sensor wells experience the enhanced flow of pre-treatment.

The pre-treatment distribution is monitored by tagging the pre-treatment oil with a fluorescent dye. The dye is then imaged using epi-fluorescence microscopy in situ.

Figure 5A:
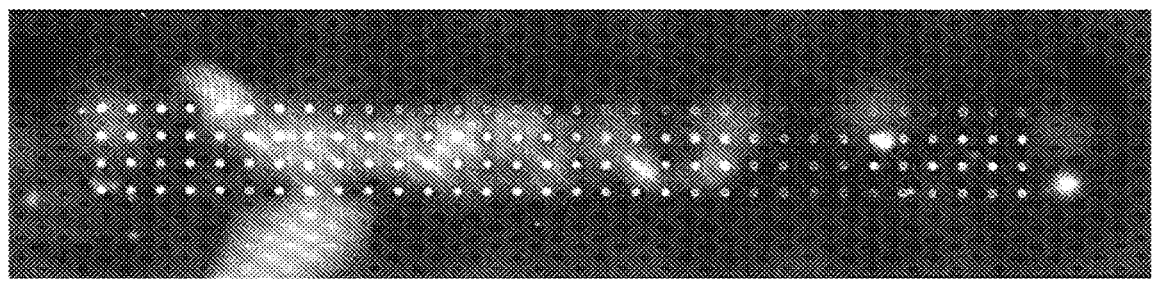
FIGS. 5a-5d are images that illustrate how changing surface design affects pre-treatment dispersal.
Figure 5B:
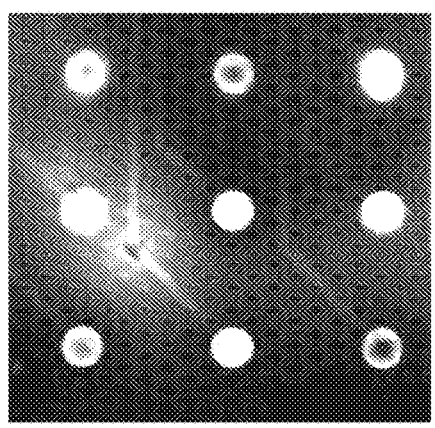
Figure 5D:
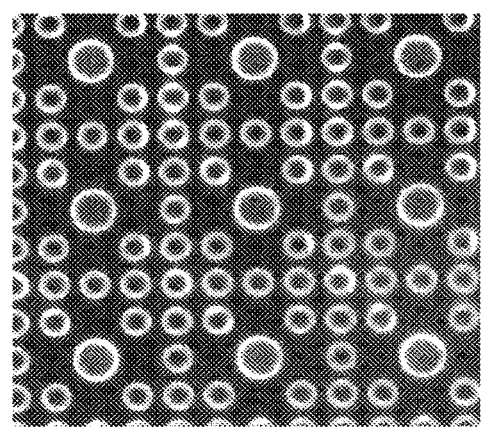
Figure 5C:
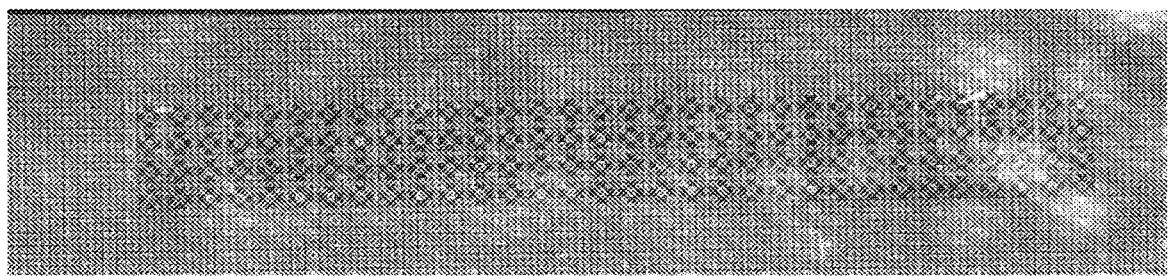

The images show in FIGS. 5a-5d show an example of the difference in distributions obtained by introducing additional wells in a surface for otherwise identical fluidic flows of pre-treatment oils dissolved in hexane over an array. FIG. 5a shows an overview of a treated array of active wells, with no additional wells, whilst FIG. 5b shows a close up view of some the wells. The bright areas indicate the presence of pre-treatment. As is particularly clear in FIG. 5b, many of the wells are completely filled by pre-treatment, and there is much excess pre-treatment on the surface. In contrast, FIG. 5c shows an overview of an array incorporating additional (smaller) inactive wells in addition to the active wells, and FIG. 5d is a close up view of some of the wells. The pre-treatment uniformly forms the 'ideal' ring structure around the wells and no wells are completely filled. Further, there is much less variation between wells in the quality of pre-treatment (even only considering non-filled wells). It is noted that the brighter areas towards the right hand side of FIG. 5c is excess pre-treatment located on the window of the cell not on the array surface (focal plane).

These images illustrate that the behaviour of fluid flowing over a surface containing wells can be influenced by changing the surface texture in between the wells. The introduced wells may, but need not, also be used as active wells. As such, if it is desired to keep a certain active well spacing, but improve the distribution of the pre-treatment, that is possible by introducing 'inactive' wells. These inactive wells help the pre-treatment flow across the surface during the application stage and further aid in the formation of a well distributed pre-treatment during the drying phase.

Exemplary experiments are discussed below.

Experimental Procedures:

Materials Required:

Clean room, Oven, RIE, Hotplate ×2, Mask aligner, Resist spinner, Develop dishes ×2, Nitrogen supply, Wafer tweezers, Inspection microscope, Silicon Wafers, SU-8 10 photoresist, SU-8 2 photoresist, EC Developer, Photolithography mask 1st layer: 4KCSH51 4201, Photolithography mask 2nd layer: 4KCSH41 4149, Acetone (propan-2-one), IPA (propan-2-ol/2-propanol).

Method for preparing wafers with well designs:

To ensure that the surfaces were clean from organic greases and salts from manufacturing and handling, silicon wafers were rinsed with acetone, 2-propanol and deionised water prior to use. The wafers were dried with a gentle supply of nitrogen. Wafers were then placed in a preheated oven for 1 hour at 150° C. The SU-8 solutions (SU-8 2, and SU-8 10) were removed from cold storage and allowed to reach room temperature prior to use. The hotplates were cleaned and allowed to reach stable temperatures of 80° C. and 110° C. The spin coater and developer dishes were set-up ready for use. SU-8 2 (9 mL) was spun onto oxygen plasma treated (200 W, 50 mTorr) wafers at 2000 rpm, which was then first placed on a hotplate at 80° C. for 1 minute prior to a 2 minute treatment on a hotplate set to 110° C. The soft-baked SU-8 2 layer was then exposed to the electrode-mask for 10 seconds, after suitable alignment to the wafer. A post exposure bake at 80° C. for 1 minute and 2 minutes at 110° C. for 2 minutes was performed. The wafer was then developed in a two-stage rinsing process, followed by a thorough rinse with 2-propanol. The wafer was dried with nitrogen prior to inspection. The wafer was then re-spun with SU-8 10 (9 mL) at 1600 rpm. The wafer was then baked again at 80° C. for 1 minute followed by 2 minutes at 110° C. The wafer was then aligned and exposed to UV for 55 seconds under the mask. A further post exposure bake of 3 minute at 80° C. followed by a second at 110° C. for 7 minutes was performed. The wafer was then developed thoroughly and washed with 2-propanol prior to a de-scumming oxygen plasma process of 1 minute. The wafers were then hard-baked at 150° C. for 1 hour. Wafers were then processed for dicing and bonding.

Diced and bonded 128 chips were then examined for surface defects prior to use. A single water wash removed surface dust particles, whilst a single ethanol wash removed surface greases prior to use.

Designs were fabricated on $SiO_2$/SU-8 with a well depth of 20 μm.

Design 1:

A standard design of 'active' wells, Design 1, is a square array of 75 μm wells, pitched at 250 μm along the X and Y axes. Pre-treatment was applied to Design 1 using by dip-coating an SU-8 and silicon piece in a pre-treatment solution of 10% pristane (2,6,10,14-tetramethylpentadecane) in hexane, at a velocity of approximately 1 mm/s.

Lipid bilayers were prepared in the following way. The micro-wells were first filled with a solution of lipid vesicles in buffer (3.6 g/L of 1,2-diphytanoyl-sn-glycero-3-phosphocholine in a buffer composed of 400 mM KCl, 25 mM Tris in water). An air-solution interface was then created by slowly retracting the excess lipid solution from the flow cell. The lipid bilayers were then painted by slowly introducing the solution of lipid in the flow cell (the optical dye sulforhodamine 101 (green excitation, red emission) was added to the lipid solution at the concentration of 0.01 g/L). The meniscus of the introduced solution effectively paints lipid bilayers on the micro-wells. The excess lipids were then flushed by a large volume of buffer.

Figure 6:
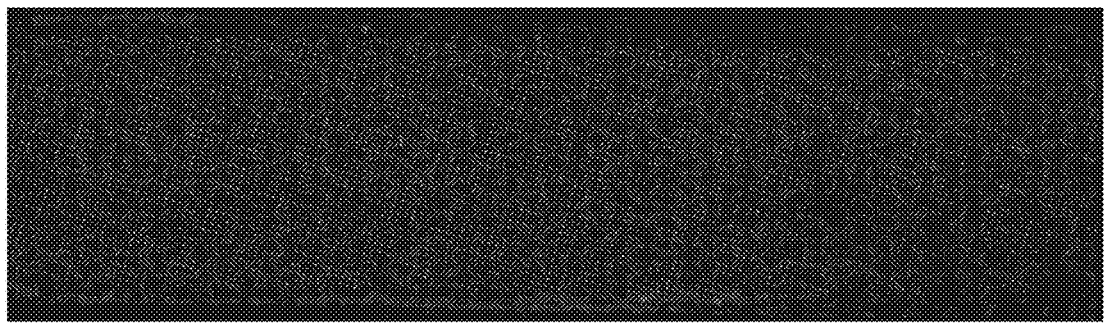
FIG. 6 is an image showing pre-treatment dispersal for a first design.

Thereafter, the presence of lipid bilayers was determined by epifluorescence, using the optical dye introduced to the lipid solution, which was trapped in the wells as the bilayer formed. A representative image, giving a general overview of the result (without particular detail of the wells), is shown in FIG. 6, in which brighter areas represent the presence of pre-treatment.

As can be seen, the quality of pre-treatment is variable, with some wells not showing the presence of any pre-treatment at all. Counting a bilayer as present if it covers a micro-well entirely, standard image processing methods of particle counting can be used to analyse the epifluorescence images. An average of 68.5% bilayer formation was found, after 3 tests, with a standard deviation of 2.7%.

To determine the effect of the design parameters on the quality of bilayer formation, further experiments were conducted.

In the following examples arrays of wells were mounted in flow cell. Pre-treatment (10% pristane in hexane, 100 μl) was pushed through the array chip at a flow rate of 100 μl/s. The chips were then dried in one of two methods. (1) By removing the connecting pipe-work and placing the array chip in a desiccator for 15 minutes under vacuum, at 200 mBar pressure (i.e. below atmospheric pressure). This allowed the hexane to evaporate leaving behind the pristane in the location it is deposited. (2) By pushing air through the array chip at a constant, but low, flow rate for 15 minutes. This allowed the hexane to evaporate at atmospheric pressure, but the vapour removed which drives the drying process.

Design 2:

The design had 75 µm wells, pitched at 250 µm along the X and Y axes. These were interleaved with the same design off set 125 µm on the X and Y axes, effectively producing a square array of 75 µm wells, pitched at 177 µm along axes angled at 45° to the X and Y axes. This design, Design 2, doubles the micro-well density on the SU-8 array compared to Design 1.

Figure 7A:
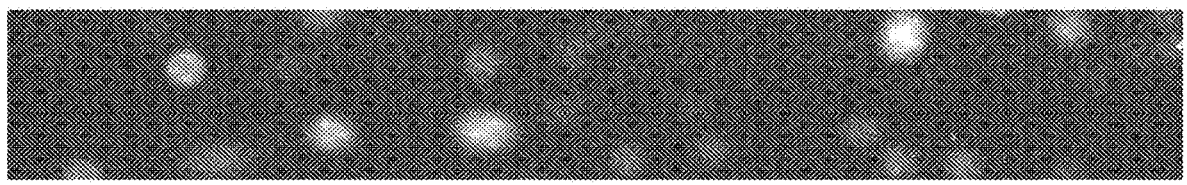
FIGS. 7a-7d are images showing pre-treatment dispersal for a second design.
Figure 7B:
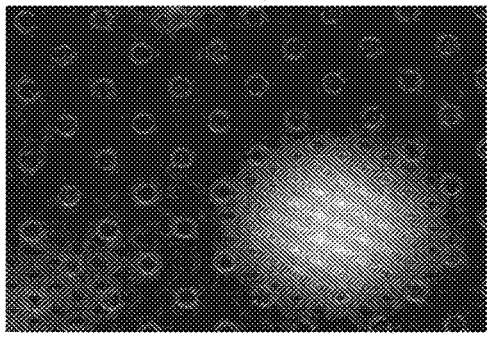
Figure 7D:
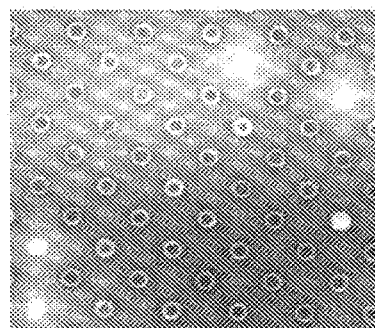
Figure 7C:
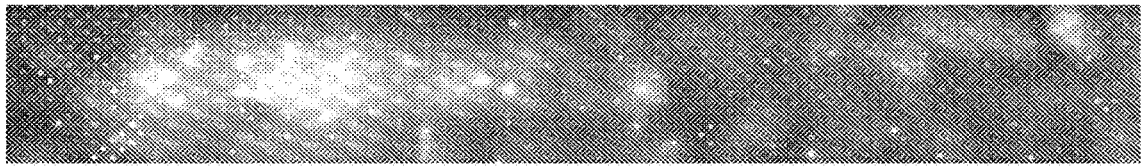

Representative images of these results are shown in FIGS. 7a-7d, in which FIG. 7a is an overview of a desiccator drying experiment (and does not provide particular detail of the wells), FIG. 7b is close up of a desiccator drying experiment, FIG. 7c is an overview of a pump drying experiment (and does not provide particular detail of the wells), FIG. 7d is a close up of a pump drying experiment.

Using the desiccator drying method, as shown in FIGS. 7a and 7b, an acceptable pre-treatment distribution was obtained. The arrays when dried in this way do not show any significant signs of pre-treatment on the surface of the SU-8 (i.e. between the micro-wells). However, it is noted that the arrays did not seem particularly even in intensity, and the overall intensity was low.

Using the pump drying method, as shown in FIGS. 7c and 7d, the results were clearly unsatisfactory. Much of the surface was covered in larger pools of pre-treatment and many of the micro-wells were filled with pre-treatment.

Figure 8A:
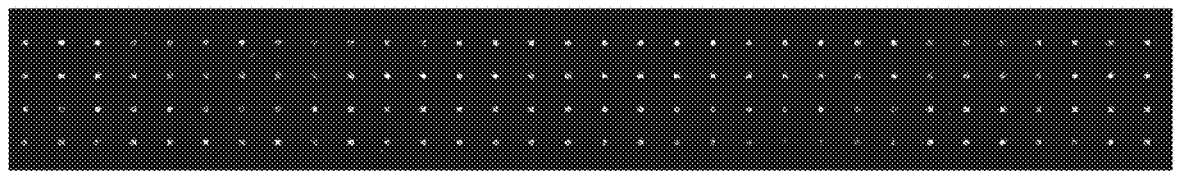
FIGS. 8a-8b are images showing pre-treatment dispersal for the second design under different conditions.
Figure 8B:
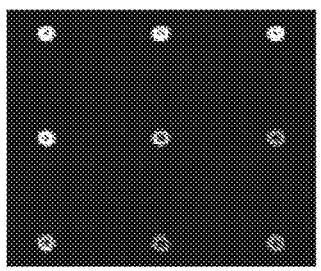

Although this may lead to the conclusion that the pre-treatment drying method is the most important factor in obtaining a good pre-treatment distribution, it is not the only consideration. As shown in FIGS. 8a and 8b, a sample produced via dip coating the pre-treatment (rather than the painting technique used for FIGS. 7a-7d), produces a satisfactory but un-even distribution, even though the surface is clear of pre-treatment. FIG. 8a is an overview of the example produced via dip coating (and does not provide particular detail of the wells), and FIG. 8b is a close up of the example produced via dip coating.

Design 3:

A design having: 75 µm wells, squarely pitched at 125 µm on both X and Y axes, was used as Design 3. This effectively represents a grid of 'active' wells as in Design 1, with an additional array of 'inactive' wells also of 75 µm diameter and squarely pitched at (0, 125 µm), (125 µm, 125 µm) and (125 µm, 0) on the X and Y axes between the 'active' wells. Design 3 increases the array density by a factor of 4 compared with Design 1.

Figure 9A:
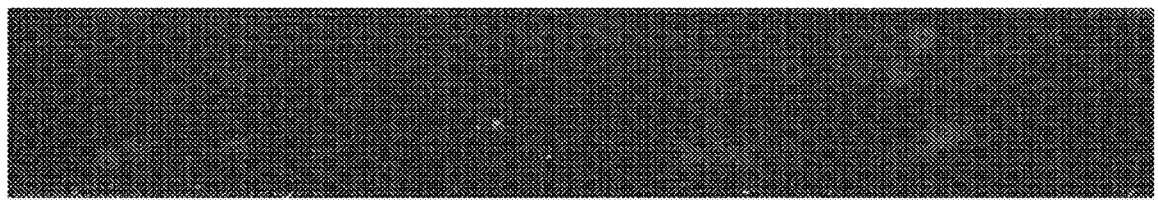
FIGS. 9a-9d are images showing pre-treatment dispersal for a third design.
Figure 9B:
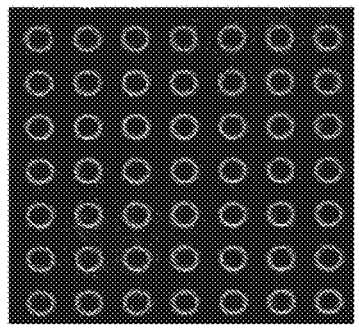
Figure 9D:
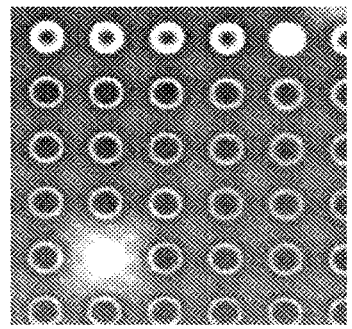
Figure 9C:

Representative images of these results are shown in FIGS. 9a-9d, in which FIG. 9a is an overview of a desiccator drying experiment (and does not provide particular detail of the wells), FIG. 9b is close up of a desiccator drying experiment, FIG. 9c is an overview of a pump drying experiment (and does not provide particular detail of the wells), FIG. 9d is a close up of a pump drying experiment. The background brightness running through FIGS. 9c and 9d is pre-treatment deposited on the top surface of the viewing cell and not on the chip surface.

As can be seen, desiccator drying resulted in the surface of the chip being completely homogeneous with respect to the pre-treatment. There is little, if any, pre-treatment sat on the SU-8 surface between the micro-wells.

Pump Drying provides an improvement over Design 2 (which has a well density half that of Design 3). However, this design still leads to significant filling of the micro-wells towards the front of the array, less so towards the rear of the chip. This is probably due to flow rate variations over the surface of the chip. Moreover, we can see the pinning effects of the micro-wells; in many cases the pre-treatment is pinned on the top SU-8 surface rather than filling the micro-wells (producing the square looking blobs between wells in FIGS. 9c and 9d). This is an unsatisfactory result.

Design 4:

Design 4 utilised wells of different shaped micro-wells, to investigate the effect the well shape has on the quality of the pre-treatment. Changing the well shape changes the aspect ratio of the area covered and also probes if any pinning is due to the shape (and symmetry) of the micro-wells.

Design 4 uses the same pitch as Design 3 (square pitch of 125 µm on both X and Y axes). However as shown in FIG. 10a, instead of an array of only circular wells (as in Design 4), an array based on the repeating pattern of one circular well and three square wells (arranged so that the four wells form a square on the array), was used as Design 4. Each circular well had a diameter of 75 µm, whilst the square wells had a side length of 75 µm.

In this design, the circular wells can be considered as representing 'active' wells, whilst the square wells represent 'inactive' wells. Therefore, Design 4 corresponds to Design 3, but with the shape of the 'inactive' wells changed.

Figure 10B:
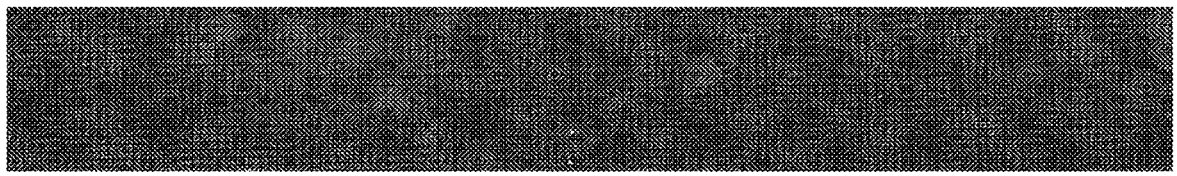
FIGS. 10b-10e are images showing pre-treatment dispersal for the fourth design.
Figure 10A:
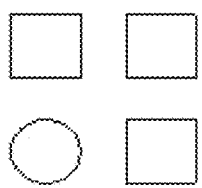
FIG. 10a is a schematic representation of a fourth design.
Figure 10C:
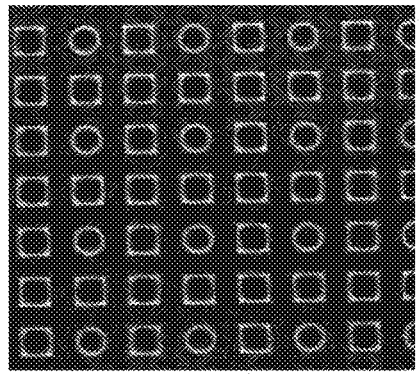
Figure 10E:
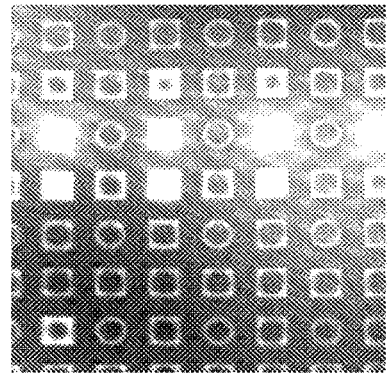
Figure 10D:
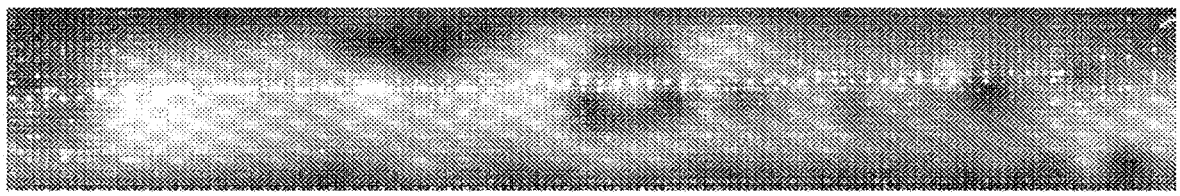

Representative images of these results are shown in FIGS. 10b-10e, in which FIG. 10b is an overview of a desiccator drying experiment (and does not provide particular detail of the wells), FIG. 10c is close up of a desiccator drying experiment, FIG. 10d is an overview of a pump drying experiment (and does not provide particular detail of the wells), FIG. 10e is a close up of a pump drying experiment. Once again, the bright background in FIGS. 10d and 10e is due to pre-treatment deposited on the view cell not on the chip surface.

As can be seen, desiccator drying provided a very similar result to the "all circular" equivalent of Design 3. The shape does not seem to affect the amount of pre-treatment remaining on the surface. That is, the change in shape does not make the quality of pre-treatment worse.

Indeed, the pump drying experiment indicates the change in shape has a positive effect. In the pump dried example (FIGS. 10d and 10e), the amount of surface remaining pre-treatment is quite high as in the "all round" counterpart. However, only the square micro-wells have filled. As a result, the quality of pre-treatment is acceptable.

Design 5:

Design 5 (shown in FIG. 11a) removes a large amount of the SU-8 surface. 75 µm circular wells are arranged on a square pitch oft 250 µm on both X and Y axes, as in Design 1. In addition, a 'background' pattern of 20 µm squares with a 5 µm boarder is provided. The use of a square background pattern, closely spaced, provides an efficient pattern for removing as much surface material as possible, whilst providing a texture.

Representative images of these results are shown in FIGS. 11b-11e, in which FIG. 11b is an overview of a desiccator drying experiment (and does not provide particular detail of the wells), FIG. 11c is close up of a desiccator drying experiment, FIG. 11d is an overview of a pump drying experiment (and does not provide particular detail of the wells), FIG. 11e is a close up of a pump drying experiment.

Once again, the bright background in FIGS. 11*d* and 11*e* is due to pre-treatment deposited on the view cell not on the chip surface.

As expected in view of the results for Designs 3 and 4, desiccator drying of Design 5 provided a surface that is very uniform and free of excess pre-treatment. The small microwells make it difficult to see the pre-treatment, but it is very uniform over the whole surface. The variation in background intensity in FIG. 11*b* is due to pre-treatment on the view cell, not the chip surface. Further, the bright area at the bottom right was found to be caused by dust on the surface, pinning more pre-treatment, but it is notable no filled wells were produced even in this region.

The pump drying experiment provided an apparently identical result (barring variations due to the presence of pre-treatment on the view-cell) to the desiccator drying experiment.

We look to the designs that we short-listed, namely the 50-81 and 50-63 (which denotes the size of the micro-patterned wells and their pitched spacing—in µms). We know that desiccator drying methods at this scale work well for both designs, since the 125 µm pitched micro-patterned wells performs well under these conditions.

Designs 6 and 7:

Designs 6 and 7 are also based upon an 'active' array of 75 µm circular wells are arranged on a square pitch oft 250 µm on both X and Y axes, as in Design 1. In addition, Design 6 (FIG. 12 *a*) incorporates a background pattern of 50 µm circular 'inactive' wells between the 'active' wells, on a square pitch of 81 µm, whilst Design 7 (FIG. 13*a*) incorporates a background pattern of 50 µm circular 'inactive' wells between the 'active' wells, on a square pitch of 63 µm. As such, in these designs the cross-sectional area of the aperture of the additional (or 'inactive' or 'flow control') wells is less than the area of the 'active' or 'sensor' wells.

Only pump drying experiments were performed for these designs, as it can be inferred from the results for Design 3 that desiccator drying will work well.

Figure 12B:
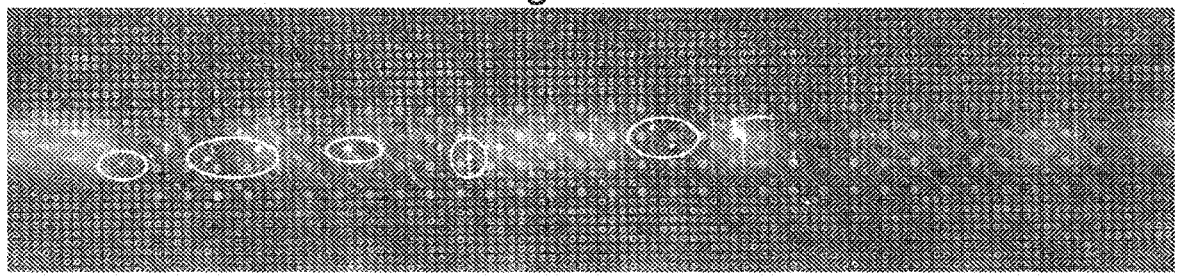
FIG. 12a is a schematic representation of a sixth design, and FIGS. 12 b and 12c are images showing pre-treatment dispersal for the sixth design.
Figure 12A:
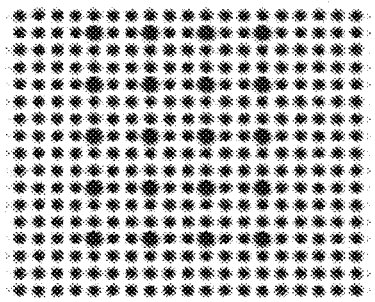
Figure 12C:
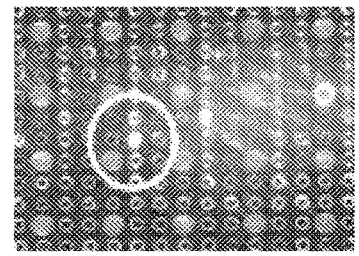
Figure 13B:
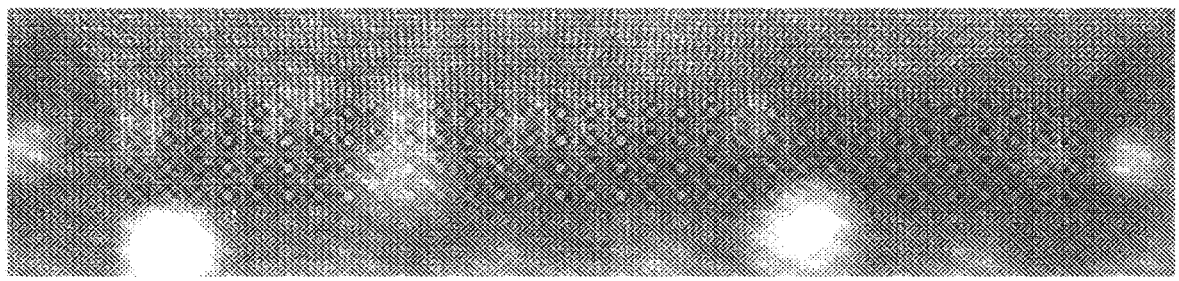
FIG. 13a is a schematic representation of a sixth design, and FIGS. 13 b and 13c are images showing pre-treatment dispersal for the seventh design.
Figure 13A:
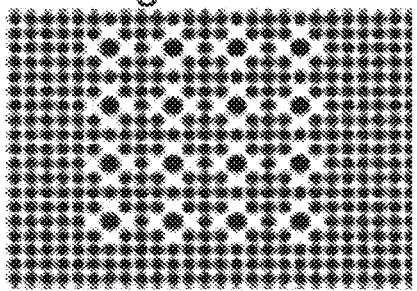
Figure 13C:
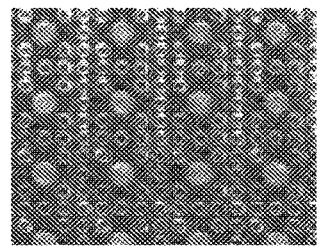

Representative images of the results for Design 6 are shown in FIGS. 12*b* and 12*c*, in which FIG. 12*b* is an overview of a desiccator drying experiment (and does not provide particular detail of the wells), and FIG. 12*c* is close up of a desiccator drying experiment. Representative images of the results for Design 7 are shown in FIGS. 13*b* and 13*c*, in which FIG. 13*b* is an overview of a desiccator drying experiment (and does not provide particular detail of the wells), and FIG. 13*c* is close up of a desiccator drying experiment.

Satisfactory results were obtained from Design 6. The majority of the surface is uniform, (there is some variation in the pre-treatment over the surface but this may be more related to the surface chemistry of the chip), however there are on average only a few micro-wells that are filled or are non-uniform compared to the majority of the micro-wells for which the pre-treatment forms in a uniform manner.

Good results were obtained from Design 7. Accounting for the obvious view cell variations, there do not appear to be any filled micro-wells, and the distribution appears to be more homogeneous compared to Design 6

The results for the above discussed designs have been quantified, and tabulated in Table 2, by allocating the quality of the pre-treatment distribution a grade. In order to do this, the homogeneity of the pre-treatment distributions were assessed by image analysis, in order to measure the rectangularity and perimeter of the pre-treatment in the wells. The rectangularity is defined as the ratio of the cross-sectional area of pretreatment to the cross-sectional area of a notional inscribed (non-rotational) rectangle within the well (i.e. the rectangle with the largest cross-sectional area which can be inscribed within the pre-treatment cross-sectional area). This ratio is pi/4 for a perfect circular object and unity for a non-rotated rectangle. To do this, the image being analysed was split into its red, green and blue components. A green fluorescent dye (a boron-dipyrromethene) was used to highlight the pretreatment and a red fluorescent dye (sulforhodamine) was used to highlight the buffer under the membrane layer. The gray-scale image was then threshold filtered just above background level. The duotone image was then subjected to a shape analysis on each object identified. On this basis the following grades were defined:

Grade 1:
the visible pre-treatment coverage of the surface is lower than 5% of the surface of the array in the fluidic cell
the number of filled wells in the array (both 'active' and 'inactive') is smaller than 0.5%
the homogeneity of the distribution of the pre-treatment annuli in the wells is high, as quantified by the rectangularity and perimeter being is within ±20% of the average value. For example, if the average value of the perimeter is 140 for a 50 µm well, then all the perimeters measured on the 50 µm wells needs to be in the interval of 112 µm to 168 µm.

Grade 2:
5%<surface coverage by pre-treatment<15%
0.5%<number of filled wells<5%
±20% of average<intervals for characteristics of the annuli<±40% of average Grade 3:
surface coverage by pre-treatment>15%
number of filled wells>5%
intervals for characteristics of the annuli>±40% of average

TABLE 2

Summary of results for Designs 2-7.

| | 'Additional' Well Diameter (µm) | X Pitch (µm) | Y Pitch (µm) | Drying Method | Grade |
|---|---|---|---|---|---|
| Design 2 | 75 | 250 | 250 | Vacuum | 2 |
| Design 2 | 75 | 250 | 250 | Pump | 3 |
| Design 3 | 75 | 125 | 125 | Vacuum | 1 |
| Design 3 | 75 | 125 | 125 | Pump | 3 |
| Design 4 | 75 (square) | 125 | 125 | Vacuum | 1 |
| Design 4 | 75 (square) | 125 | 125 | Pump | 2 |
| Design 5 | 15 (square) | 5 | 5 | Vacuum | 1 |
| Design 5 | 15 (square) | 5 | 5 | Pump | 1 |
| Design 6 | 50 | 81 | 81 | Pump | 2 |
| Design 7 | 50 | 63 | 63 | Pump | 1 |

As can be seen from Table 2, and the forgoing discussion, vacuum/desiccator drying provides better quality distributions for similar well geometries than pump/convection drying for less textured (i.e. having larger, more spaced apart additional wells) surfaces. However, for highly textured surfaces the drying method does not affect the grade of pre-treatment obtained (i.e. as shown by Design 5).

It can also be seen that is preferable to have more closely spaced 'additional' wells (e.g. by comparing Designs 2 and 3), to obtain better quality pre-treatment distribution. Preferably the additional wells are spaced at 125 µm apart or less, more preferably 100 µm apart or less, more preferably 81 µm or less, more preferably 63 µm or less. Preferably, the pitch of the additional wells is smaller than the pitch of the array of 'sensor' or 'active' wells.

It is also possible to calculate the number density of wells (wells/micron$^2$), area density of wells (well area/total area), nearest-neighbour distance between wells for the Designs 1 to 3. These designs represent designs have only one shape of well is present (both in terms of geometry and size). These values are quantified in Table 3.

TABLE 3

Bulk characteristics of Designs 1-3

| | Well Number Density (wells/micron$^2$) | Well Area Density (—) | Well Nearest Neighbour Distance (microns) |
|---|---|---|---|
| Design 1 | $1.6 \times 10^{-5}$ | 0.071 | 175 |
| Design 2 | $3.2 \times 10^{-5}$ | 0.141 | 102 |
| Design 3 | $6.4 \times 10^{-5}$ | 0.283 | 50 |

From the trends in Tables 2 and 3, it is apparent that it is preferable to have a higher density of wells on the surface to provide a better pre-treatment distribution. Preferably, the number distribution of wells (whether active or inactive) is at least $3.2 \times 10^{-5}$ wells/micron$^2$, more preferably $6.4 \times 10^{-5}$ wells/micron$^2$. Preferably, the well area density is 0.141 or more, more preferably 0.283 or more. Preferably the wells are formed so that the distance to the next nearest well is 102 microns away or less, more preferably 50 microns or less.

It is also contemplated that future apparatuses may reduce further in size, in which case the 'additional' wells provided in Designs 6 and 7, may actually be used as a continuous array of active wells. In that case, the Designs would have the characteristics shown in Table 4.

TABLE 4

Bulk characteristics of 'additional' wells of Designs 6 and 7

| | Well Number Density (wells/micron$^2$) | Well Area Density (—) | Well Nearest Neighbour Distance (microns) |
|---|---|---|---|
| Design 6 | $1.5 \times 10^{-4}$ | 0.299 | 31 |
| Design 7 | $2.5 \times 10^{-4}$ | 0.495 | 13 |

As such, the number distribution of wells is still more preferably $1.5 \times 10$ wells/micron$^2$ or more, and still more preferably $2.5 \times 10$ wells/micron$^2$ or more. Further the well area density is still more preferably 0.299 or more, and still more preferably 0.495 or more. Additionally, the wells are still more preferably formed so that the next nearest well is 31 microns away or less, and more preferably 13 microns away or less.

It is further apparent from Table 1 that is preferable for the wells, whether they are all active or not, to be smaller. Preferably the wells are 75 microns in diameter or smaller, more preferably 50 microns in diameter or smaller.

In practice, the advantage of the present invention may be achieved using arrays constructed either only partially or entirely of active wells. By controlling the surface energy by using the additional wells (whether they are ultimately used for sensing or otherwise) an improved flow of the pre-treatment can be obtained as well as an improvement of the subsequent pre-treatment distribution. Even in the absence of a pre-treatment step, the improved flow control gives more uniform flows that can help bilayer formation.

The present invention has been described above with reference to specific embodiments. It will be understood that the above description does not limit the present invention, which is defined in the appended claims.

The invention claimed is:

1. An apparatus for supporting an array of layers of amphiphilic molecules, the apparatus comprising:
   (A) a body;
   (B) formed in the body, an array of sensor wells and, between the sensor wells, flow control wells,
   wherein a common surface of the body defines openings to the sensor wells and openings to the flow control wells,
   wherein the sensor wells are capable of supporting a layer of amphiphilic molecules across the sensor wells,
   wherein the sensor wells each contain an electrode for connection to an electrical circuit, and
   wherein the flow control wells are capable of smoothing the flow of a fluid across the common surface; and
   (C) formed in the body, surface patterning on a second surface that extends beyond the common surface of the body, wherein the surface patterning is configured to provide uniform flow of the fluid to the common surface;
   and
   wherein the cross-sectional area of a flow control well is less than the cross-sectional area of a sensor well.

2. An apparatus according to claim 1, further comprising a cover over the common surface and the second surface of the body defining a cavity between the cover and the common surface and second surface, and a common electrode arranged in the cavity for connection to the electrical circuit.

3. An apparatus according to claim 2, wherein the cover has an internal surface, facing the common surface and the second surface of the body, that is roughened to smooth the flow of fluid thereover.

4. An apparatus according to claim 3, wherein the internal surface is roughened with surface patterning.

5. An apparatus according to claim 1, wherein the array of sensor wells is a regular array, and the flow control wells consist of a regular array of flow control wells.

6. An apparatus according to claim 5, wherein the pitch of at least a portion of the regular array of flow control wells is smaller than the pitch of at least a portion of the regular array of sensor wells.

7. An apparatus according to claim 1, wherein the sensor wells are circular and/or wherein the flow control wells have a different shape.

8. An apparatus according to claim 1, wherein the sensor wells are circular and/or wherein the flow control wells are square.

9. An apparatus according to claim 1, wherein the sensor wells, the flow control wells, and/or the surface patterning are arranged such that a pre-treatment of a hydrophobic fluid applied to the common surface of the body and/or the second surface of the body would not enter the Cassie-Baxter state.

10. An apparatus according to claim 1, wherein the sensor wells and flow control wells are shaped to provide:
   i) a surface roughness r, defined as the total area of the surface and wells divided by the projected area of the surface, and
   ii) a φ, defined as the area of the surface between the wells divided by the projected area of the surface,
   that meet the requirement $((\varphi-1)/(r-\varphi)) > \cos \theta$ for a pre-treatment applied to the common surface of the body,
   wherein, with respect to the body, the pre-treatment has a contact angle θ, and
   wherein the pre-treatment is a fluid that is capable of interacting with the amphiphilic molecules.

11. An apparatus according to claim 1, wherein the array of sensor wells is formed in the body with a number density of $6.4 \times 10^{-5}$ sensor wells/micron$^2$ or more.

12. An apparatus according to claim 1, wherein the array of sensor wells is formed in the body with a number density of $1.5 \times 10^{-4}$ sensor wells/micron$^2$ or more.

13. An apparatus according to claim 1, wherein the array of sensor wells is formed in the body with a number density of $2.5 \times 10^{-4}$ sensor wells/micron$^2$ or more.

14. An apparatus according to claim 1, further comprising a pre-treatment, that is a fluid capable of interacting with the amphiphilic molecules, applied to the sensor wells.

15. An apparatus according to claim 1, wherein the surface patterning comprises second flow control wells, wherein the second surface of the body defines openings to the second flow control wells.

16. An apparatus according to claim 15, wherein the second flow control wells consist of a regular array of second flow control wells.

17. An apparatus according to claim 1, wherein the sensor wells have a number density of $3.2 \times 10^{-5}$ sensor wells/micron$^2$ or more.

\* \* \* \* \*